US010238380B2

(12) United States Patent
Kawaura et al.

(10) Patent No.: US 10,238,380 B2
(45) Date of Patent: Mar. 26, 2019

(54) MEDICAL TUBE, MEDICAL TUBE ASSEMBLY, AND INTRAPELVIC TREATMENT KIT

(71) Applicant: TERUMO KABUSHIKI KAISHA, Shibuya-ku, Tokyo (JP)

(72) Inventors: Masakatsu Kawaura, Sunnyvale, CA (US); Nao Yokoi, Sunnyvale, CA (US); Shigeki Ariura, Ebina (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 475 days.

(21) Appl. No.: 14/873,048

(22) Filed: Oct. 1, 2015

(65) Prior Publication Data

US 2016/0022262 A1 Jan. 28, 2016

Related U.S. Application Data

(63) Continuation of application No. PCT/JP2013/059898, filed on Apr. 1, 2013.

(51) Int. Cl.
*A61B 17/04* (2006.01)
*A61B 17/34* (2006.01)
(Continued)

(52) U.S. Cl.
CPC .... *A61B 17/0482* (2013.01); *A61B 17/06109* (2013.01); *A61B 17/3468* (2013.01);
(Continued)

(58) Field of Classification Search
CPC .... A61B 17/06066; A61B 2017/00805; A61B 17/0482; A61B 17/06109; A61B 17/062;
(Continued)

(56) References Cited

U.S. PATENT DOCUMENTS 4,392,495 A * 7/1983 Bayers .................. A61B 17/04
128/898
5,112,344 A * 5/1992 Petros ................ A61B 17/0469
128/DIG. 25
(Continued)

FOREIGN PATENT DOCUMENTS

EP 0317091 A2 5/1989
JP 2010-099499 A 5/2010

OTHER PUBLICATIONS

International Search Report (PCT/ISA/210) dated May 28, 2013, by the Japanese Patent Office as the International Searching Authority for International Application No. PCT/JP2013/059898.
(Continued)

*Primary Examiner* — Kaylee R Wilson
(74) *Attorney, Agent, or Firm* — Buchanan Ingersoll & Rooney PC

(57) ABSTRACT

A medical tube is disclosed, which includes a tubular main body curved in a circular arc shape. The main body has a flat shape as a cross-sectional shape at a central portion in the longitudinal direction thereof. The main body has a flat shape including a minor axis and a major axis as a cross-sectional shape at the central portion in the longitudinal direction thereof. The angle formed between the minor axis and a plane containing both a center point of the circular arc in the central portion and a center point of the cross-sectional shape with respect to the longitudinal direction of the main body is an acute angle. The angle is preferably 20° to 60°. The medical tube thus configured is for use in treatment of a disorder in a pelvic organ, by indwelling an implant between a urethral lumen and a vaginal cavity.

14 Claims, 36 Drawing Sheets

(51) Int. Cl.
*A61B 17/06* (2006.01)
*A61F 2/00* (2006.01)
*A61M 1/00* (2006.01)
*A61B 17/00* (2006.01)
*A61B 17/30* (2006.01)

(52) U.S. Cl.
CPC .. *A61F 2/0045* (2013.01); *A61B 2017/00805* (2013.01); *A61B 2017/061* (2013.01); *A61B 2017/0608* (2013.01); *A61B 2017/06042* (2013.01); *A61B 2017/06047* (2013.01); *A61B 2017/06052* (2013.01); *A61B 2017/06104* (2013.01); *A61B 2017/306* (2013.01); *A61B 2017/3405* (2013.01); *A61F 2/005* (2013.01); *A61M 1/008* (2013.01)

(58) Field of Classification Search
CPC ...... A61B 17/3468; A61B 2017/06052; A61B 17/3403; A61B 17/42; A61F 2002/0072; A61F 2/0045; A61F 2/0063
See application file for complete search history.

(56) References Cited

U.S. PATENT DOCUMENTS

| | | |
|---|---|---|
| 2003/0125789 A1* | 7/2003 | Ross .................. A61F 2/95 623/1.11 |
| 2003/0171644 A1 | 9/2003 | Anderson et al. |
| 2004/0087970 A1* | 5/2004 | Chu ................ A61B 17/00234 606/119 |
| 2008/0091058 A1 | 4/2008 | Bosley et al. |
| 2008/0242917 A1* | 10/2008 | Kaladelfos ......... A61B 17/0469 600/30 |
| 2009/0112258 A1 | 4/2009 | Kreider |
| 2012/0197281 A1 | 8/2012 | Chu |

OTHER PUBLICATIONS

Written Opinion (PCT/ISA/237) dated May 28, 2013, by the Japanese Patent Office as the International Searching Authority for International Application No. PCT/JP2013/059898.

Extended European Search Report dated Jul. 13, 2017 in corresponding European Patent Application No. 13880701.1.

* cited by examiner

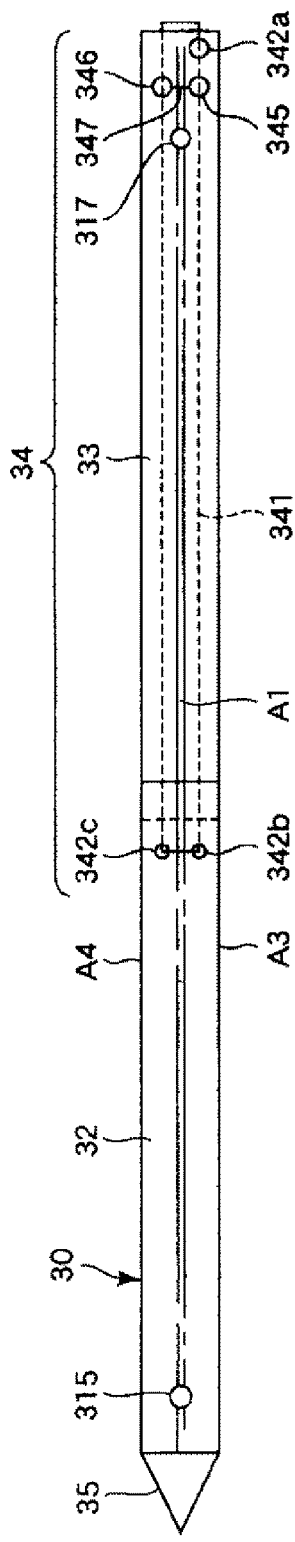
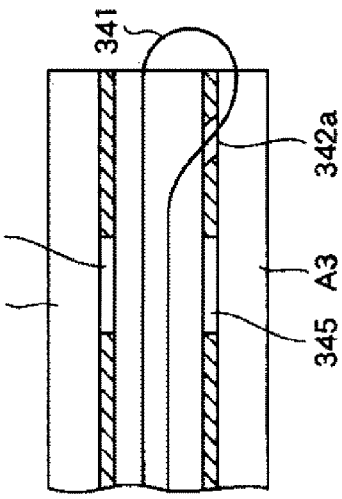
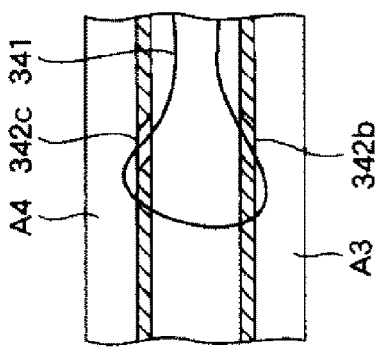
FIG. 6a
FIG. 6c
FIG. 6b

MEDICAL TUBE, MEDICAL TUBE ASSEMBLY, AND INTRAPELVIC TREATMENT KIT

CROSS-REFERENCES TO RELATED APPLICATIONS

This application is a continuation of International Application No. PCT/JP2013/059898 filed on Apr. 1, 2013, the entire content of which is incorporated herein by reference.

TECHNICAL FIELD

The present disclosure generally relates to a medical tube, a medical tube assembly, and an intrapelvic treatment kit.

BACKGROUND DISCUSSION

If a person suffers from a urinary incontinence, for example, if a person suffers from a stress urinary incontinence, then urine leakage can be caused by application of abdominal pressure during normal exercise or by laughing, coughing, or sneezing. The cause of this may be, for example, that the pelvic floor muscle which is a muscle for supporting the urethra is loosened by birth.

For the treatment of urinary incontinence, a surgical treatment is effective, in which there is used, for example, a belt-shaped implant called "sling." The sling is indwelled inside the body and the urethra is supported by the sling (see, for example, Japanese Patent Laid-open No. 2010-99499). In order to indwell the sling inside the body, an operator would incise the vagina with a surgical knife, dissect the part between the urethra and vagina, and make the dissected region and the outside communicate with each other through obturator foramens by use of a puncture needle. Then, in this state, the sling is indwelled into the body.

If the vaginal wall is incised once, however, a situation may occur that the sling is exposed to the inside of the vagina from a wound caused by the incision of the vaginal wall, and complications may cause an infection from the wound. Further, since the vaginal wall is incised, there is such a defect that the invasion is relatively great and the burden on the patient is relatively heavy. Further, the urethra may be damaged by a surgical knife in the course of the procedure by the operator. In addition, the fingertip of the operator himself/herself may be damaged or injured by the surgical knife.

SUMMARY

A medical tube, a medical tube assembly, and an intrapelvic treatment kit are disclosed by which an implant can be placed indwelling in a living body in such a posture as to be able to exhibit its function relatively effectively.

A medical tube is disclosed, which can include a tubular main body having a curved central portion, the medical tube characterized in that at least part of the central portion has a circular arc shape and the main body has a flat shape including a minor axis and a major axis as a cross-sectional shape at the central portion, and the angle formed between the minor axis and a plane containing both a center point of the circular arc in the central portion and a center point of the cross-sectional shape with respect to the longitudinal direction of the main body is an acute angle.

The medical tube as disclosed, wherein the angle is 20° to 60°.

The medical tube as disclosed, to be used in treatment of a disease in a pelvic organ by leaving an implant indwelling between a urethral lumen and a vaginal cavity.

A medical tube assembly is disclosed, which can include the medical tube as disclosed; and an elongated insertion section to be inserted into the main body, characterized in that the medical tube assembly is used in a state where the insertion section is inserted in the main body.

A medical tube is disclosed for use in intrapelvic treatment, characterized in that: the medical tube can include a tubular main body having an internal space in which a belt-shaped elongated article can be inserted, the main body having a curved central portion; the medical tube can include a circular arc section where at least part of the central portion has a circular arc shape; the main body has a flat shape including a minor axis and a major axis as a cross-sectional shape at the central portion; and a center axis of the circular arc of the circular arc shape and an extension line of the major axis have an intersection.

The medical tube as disclosed, wherein the angle formed between the center axis and the extension line is an acute angle.

The medical tube as disclosed, wherein the angle is 20° to 60°.

The medical tube as disclosed, characterized in that the main body is formed from a rigid material capable of maintaining the internal space in a state where the main body is inserted in a body.

A medical tube is disclosed, which can include a tubular main body having a curved central portion, the medical tube characterized in that the central portion is provided at least at part of the central portion with a circular arc section having a circular arc shape, the circular arc section has an outer circumferential portion located at an outer circumferential edge of the circular arc section and an inner circumferential portion located at an inner circumferential edge of the circular arc section, in plan view as viewed along a center axis direction of the circular arc section and the outer circumferential portion and the inner circumferential portion are spaced apart from each other in the center axis direction.

The medical tube as disclosed, wherein the cross-sectional shape of the circular arc section is a flat shape including a minor axis and a major axis, and the outer circumferential portion is located at one end of the major axis, and the inner circumferential portion is located at the other end.

An intrapelvic treatment kit is disclosed, which can include an implant main body having a width and a length and a medical tube including a main body which is tubular in shape, the main body having a curved central portion and an internal space, the central portion having a circular arc shape at least at part of the central portion, and the main body having a flat cross-sectional shape at the central portion which can include a minor axis and a major axis such that the length of the major axis in the internal space is shorter than the width.

A method is disclosed for treatment of a disease in a pelvic organ by leaving an implant indwelling between a urethral lumen and a vaginal cavity, the method comprising: inserting a medical tube into a living body, the medical tube having a tubular main body having a curved central portion, at least part of the central portion has a circular arc shape, and the main body has a flat shape including a minor axis and a major axis as a cross-sectional shape at the central portion, and an angle formed between the minor axis and a plane containing both a center point of the circular arc in the central portion and a center point of the cross-sectional shape with respect to the longitudinal direction of the main body is an acute angle; inserting an implant main body into the internal space of the medical tube; removing the medical tube from the living body; and embedding the implant main body in the living body between the urethral lumen and the vaginal cavity.

In the present disclosure, the angle formed between the above-mentioned minor axis and the plane (hereinafter referred to as "the above-mentioned plane") containing both the center point of the circular arc in the central portion of the main body and the center point of the cross-sectional shape with respect to the longitudinal direction of the main body is an acute angle. For example, in the case where the main body is disposed in the living body in the manner of sequentially passing the obturator foramen on one side, between the urethra and vagina, and the obturator foramen on the other side, the insertion of the main body into the living body can be carried out relatively easily and safely by a method in which the angle formed between the above-mentioned plane and a plane orthogonal to the axis of the urethra is set to be an acute angle (at the same degree as the above-mentioned angle). Therefore, when the angle formed between the above-mentioned plane and the above-mentioned minor axis is set to be an acute angle, the main body can be disposed inside the living body in such a manner that the major axis direction of the cross section thereof is substantially parallel to the urethra. As a result, the implant inserted in the main body can also be disposed substantially in parallel to the urethra. Thus, according to the present disclosure, the implant can be placed indwelling in the living body in such a posture as to be able to exhibit its function effectively.

BRIEF DESCRIPTION OF THE DRAWINGS

FIG. 6(a) is a top plan view of a state maintaining mechanism possessed by the puncture member shown in FIG. 4(a).

FIGS. 6(b) and 6(c) are sectional views of a state maintaining mechanism possessed by the puncture member shown in FIG. 4(a).

FIGS. 7(a)-7(c) show a partial enlarged view depicting a state maintaining mechanism possessed by the puncture member shown in FIG. 3, wherein FIG. 7(a) and FIG. 7(b) are each plan views showing modifications, and FIG. 7(c) is a plan view showing the present embodiment.

FIGS. 8(a) and 8(b) illustrate a second anchor possessed by the puncture device shown in FIG. 1, wherein FIG. 8(a) is a sectional view, and FIG. 8(b) is a sectional view showing a condition where the second anchor is engaged with the puncture member.

FIGS. 9(a)-9(b) illustrate a first anchor possessed by the puncture device shown in FIG. 1, wherein FIG. 9(a) is a sectional view, and FIG. 9(b) is a sectional view showing a condition where the first anchor is engaged with the puncture member.

FIGS. 15(a)-15(b) illustrate a positional relation of the puncture member and an obturator foramen (pelvis), wherein FIG. 15(a) is a side view and FIG. 15(b) is a front view.

FIGS. 33(a)-33(c) illustrate a medical tube (medical tube assembly) according to a seventh embodiment of the present disclosure, wherein FIG. 33(a) is a plan view, and FIG. 33(b) and FIG. 33(c) are each sectional views.

FIGS. 36(a)-36(c) illustrate a medical tube (medical tube assembly) according to a ninth embodiment of the present disclosure, wherein FIG. 36(a) is a plan view, and FIGS. 36(b) and 36(c) are each sectional views.

DETAILED DESCRIPTION

A medical tube, a medical tube assembly, and an intrapelvic treatment kit of the present disclosure will be described in detail below, based on preferred embodiments illustrated in the attached drawings.

Figure 2:
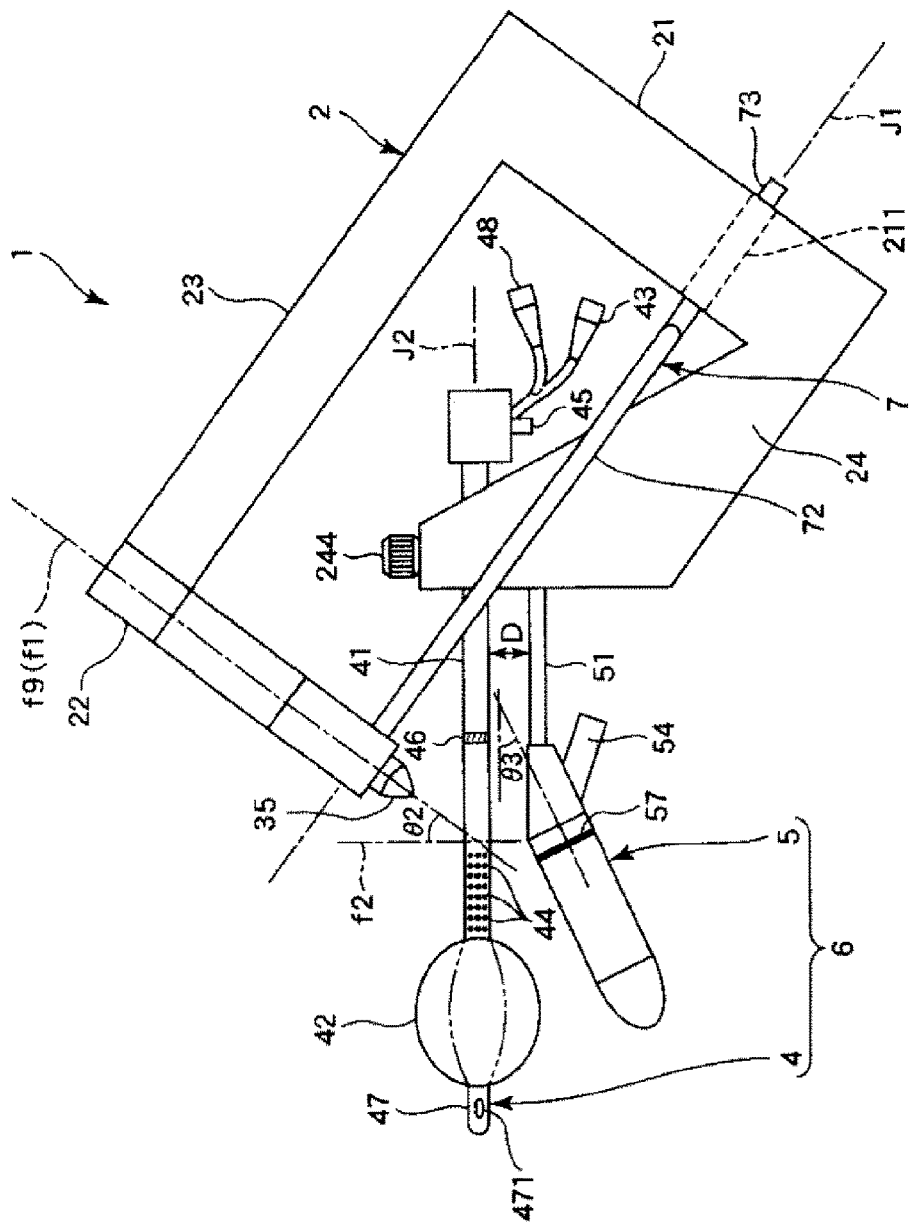
FIG. 2 is a side view of the puncture device shown in FIG. 1.

Note that in the following, for convenience of explanation, the left side in FIG. 2 will be referred to as "distal end," the right side as "proximal end," the upper side as "up," and the lower side as "down." FIG. 2 shows a puncture device in the state of not yet used, and this state will be referred to as the "initial state" for convenience of explanation. In accordance with an exemplary embodiment, a state where the puncture device (insertion tool) shown in FIG. 2 is mounted onto a patient will be referred to also as the "mounted state." Further, in each of FIGS. 5 and 6, a puncture member extending in a circular arc shape is depicted in the state of being stretched rectilinearly, for convenience of explanation.

First, a puncture device to which a medical tube and a medical tube assembly of the present disclosure are applied will be described.

Figure 1:
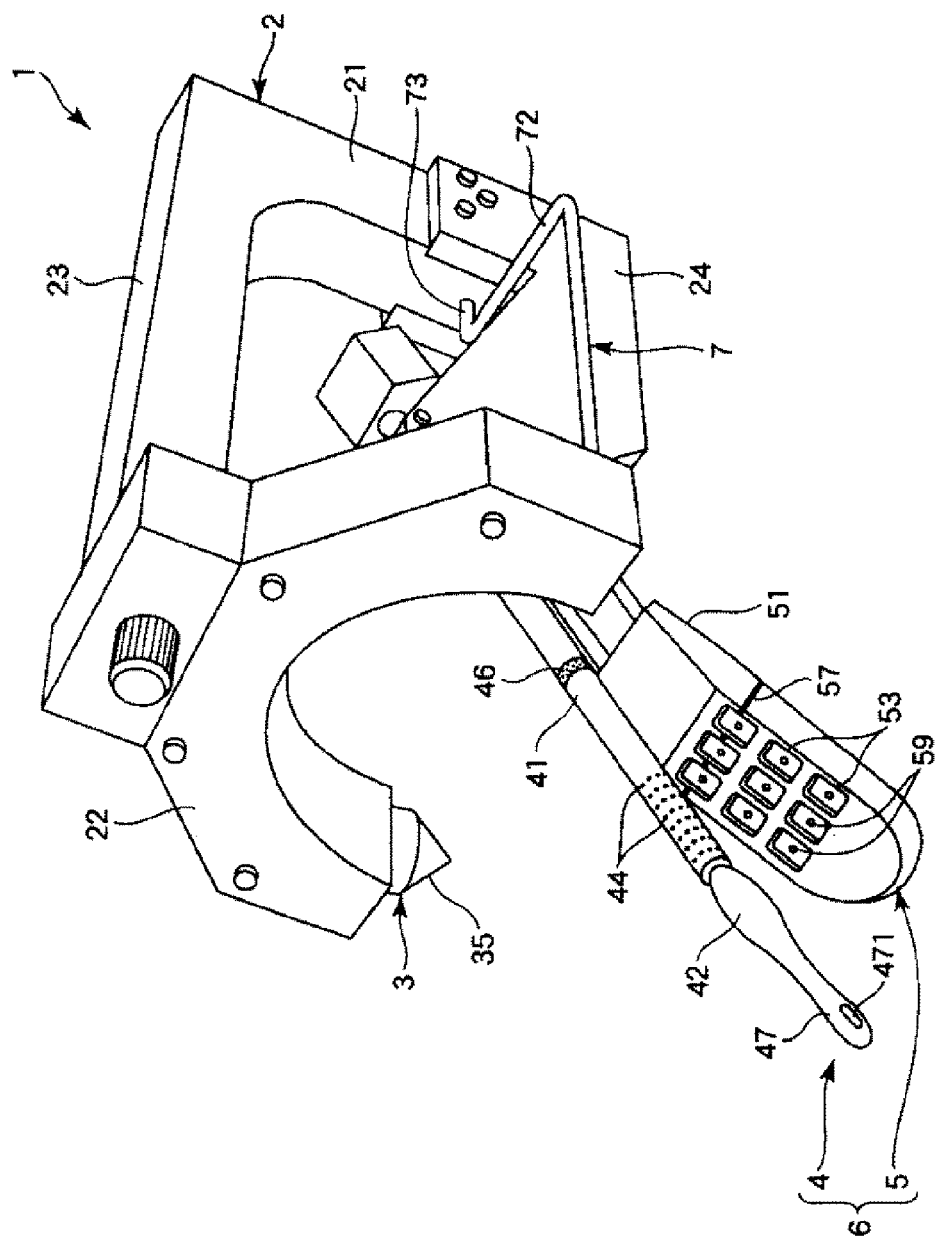
FIG. 1 is a perspective view showing a puncture device to which a medical tube (medical tube assembly) according to a first embodiment of the present disclosure is applied.

A puncture device 1 shown in FIGS. 1 and 2 is a device for use in treatment of female urinary incontinence, for example, in embedding (implanting) in a living body a biological tissue supporting indwelling article for treatment of urinary incontinence.

This puncture device 1 can include a frame (support section) 2, a puncture member 3, a urethral-insertion member 4, a vaginal-insertion member 5, an operating member 7 and anchors 81 and 82. The puncture member 3, the urethral-insertion member 4, the vaginal-insertion member 5, the operating member 7 and the anchors 81 and 82 are each supported by the frame 2. In accordance with an exemplary embodiment, in the puncture device 1, the urethral-insertion member 4 and the vaginal-insertion member 5 constitute an insertion tool 6. These will be sequentially described below.

Figure 3:
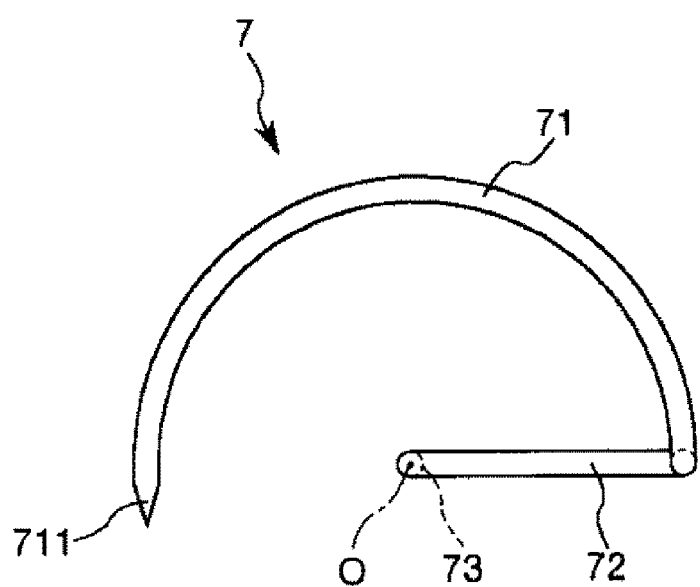
FIG. 3 is a plan view showing an operating member possessed by the puncture device shown in FIG. 1.

The operating member 7 is a member for operating the puncture member 3. As shown in FIGS. 1 to 3, such an operating member 7 can include an insertion section 71, a shaft section 73, and an interlock section 72 interlocking the insertion section 71 and the shaft section 73. The insertion member 71, the interlock section 72 and the shaft section 73 may be formed to be integral with one another, or, alternatively, at least one of them may be formed as a separate body from the others of them.

The insertion section 71 is a part to be inserted into the puncture member 3, and functions as a stylet for reinforcing the puncture member 3 internally. With the insertion section 71 inserted in the puncture member 3, the puncture member 3 is connected to the operating member 7, whereby an operation of the puncture member 3 by the operating member 7 is enabled. The insertion member 71 as above has a circular arc shape corresponding to the shape of the puncture member 3. The center angle of the insertion member 71 is set in accordance with the center angle of the puncture member 3. A distal portion 711 of the insertion section 71 is tapered off. With the tapered-off distal portion 711 provided, the insertion of the puncture member 3 into the insertion section 71 can be performed smoothly.

The shaft section 73 extends along an axis J1 which intersects the center O of the insertion section 71 and is orthogonal to a plane f1 containing the insertion section 71.

The interlock section 72 interlocks a proximal portion of the insertion section 71 and a distal portion of the shaft section 73. The interlock section 72 has a substantially L-shaped form of being bent substantially at right angle at an intermediate portion thereof. The interlock section 72 functions also as a grip section to be gripped by an operator at the time of operating the operating member 7.

The operating member 7 as above is configured to be higher in rigidity than the puncture member 3 (main body 31). The material constituting the operating member 7 is not particularly limited; there can be used, for example, various metallic materials such as stainless steel, aluminum or aluminum alloys, titanium or titanium alloys, etc.

Figure 4A:
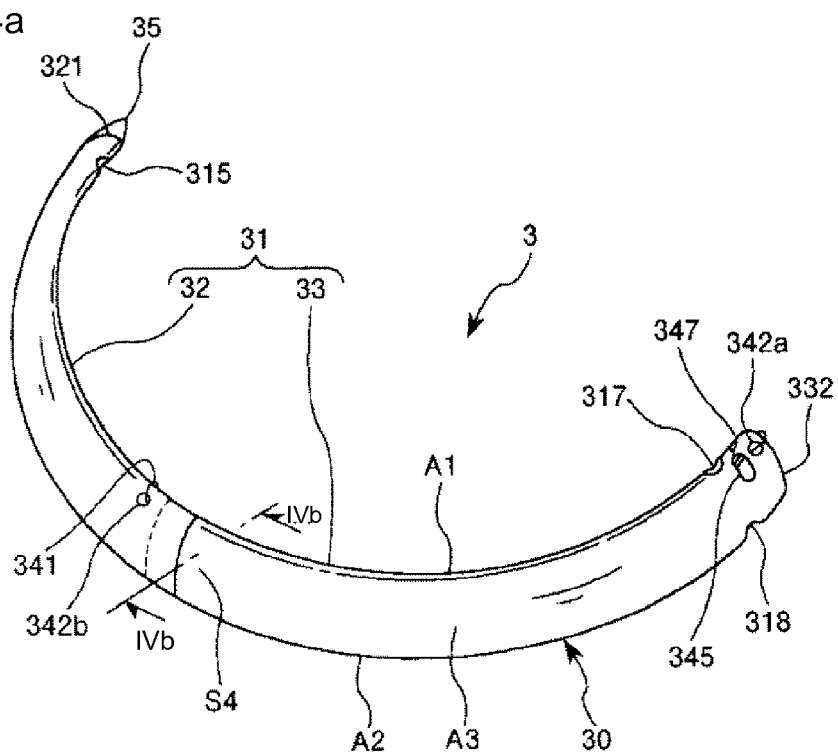
FIG. 4(a) is a perspective view of a puncture member possessed by the puncture device shown in FIG. 1.

The puncture member 3 is a member for puncturing a living body. As shown in FIG. 4(a), such a puncture member 3 can include an elongated sheath (medical tube) 30, and a needle body 35 provided at the distal end of the sheath 30. The sheath 30 can include the main body 31, which is tubular in shape, and a state maintaining mechanism 34.

Figure 4B:
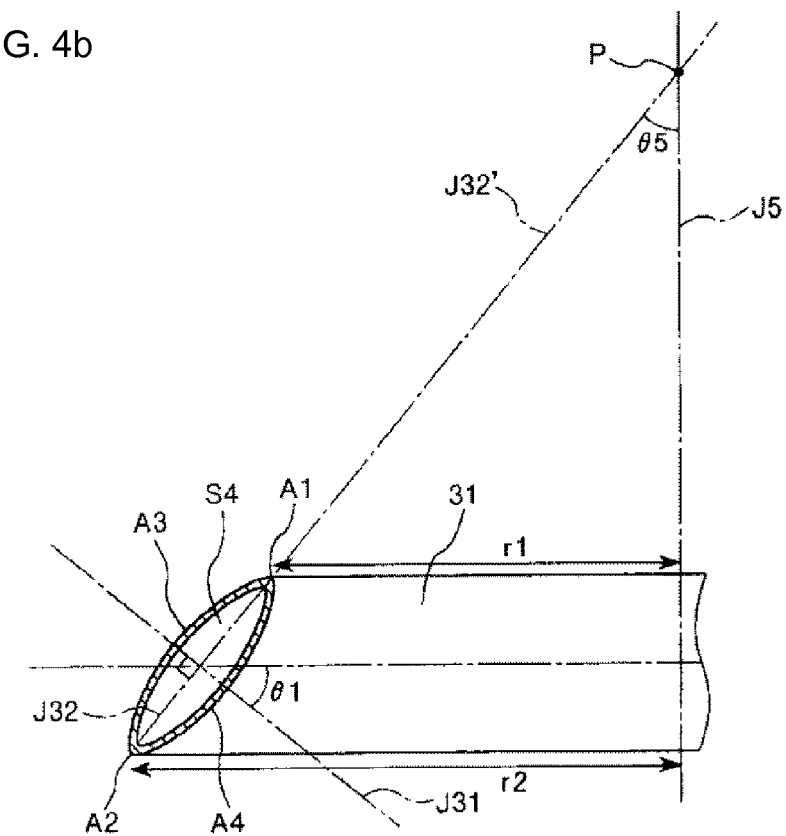
FIG. 4(b) is a sectional view taken along line IXb-IXb of FIG. 4(a).

The main body 31 can include an elongated tubular body (tube), opening at both the distal end and the proximal end thereof. Such a main body 31 has an internal space in which an implant main body 91 can be inserted. The main body 31 has a bent shape of being bent in a circular arc shape, and is flat shaped in cross section as shown in FIG. 4(b). For example, the cross-sectional shape at a central portion S4 in the longitudinal direction of the main body 31 is a flat shape including a minor axis J31 and a major axis J32. As will be described later, the implant main body 91 is disposed inside the main body 31. With the main body 31 flat shaped, therefore, the posture of the implant main body 91 within the main body 31 can be controlled.

In addition, the width (the length in the direction of the major axis J32) of the internal space of the main body 31 is designed to be substantially the same as the width of a main body section 911 (described later) of the implant main body 91, which can help ensure that even when the implant main body 91 is moved, the frictional resistance with the internal space of the main body 31 is low, so that no unnecessary force is exerted on the implant main body 91, and the main body section 911 can be disposed in a sufficiently developed state within the main body 31. Note that the width (the length in the direction of the major axis J32) of the internal space of the main body 31 may be shorter than the width of the main body section 911. As a result, the width of the main body 31 can be restrained from becoming large, so that a less invasive puncture member 3 can be realized.

Note that the flat shape of the main body 31 is not specifically restricted; for example, ellipses, convex lens-like shapes in section, rhombuses with corners rounded, rectangles (flat shapes) with corners rounded, and spindle-like shapes with a central portion enlarged (enlarged in diameter) as compared with both end portions may be adopted as the flat shape.

In the following, for convenience of explanation, an end portion located on the inner side (one end) in the direction of the major axis J32 will be referred to also as an "inner circumferential portion A1," an end portion located on the outer side (other end) will be referred to also as an "outer circumferential portion A2," a surface oriented toward the upper side will be referred to also as a "front surface A3," and a surface oriented toward the lower side will be referred to also as a "back surface A4," as shown in FIG. 4(b).

As shown in FIG. 4(b), let a plane containing both the center point of the circular arc of the central portion S4 and the center point of the cross-sectional shape with respect to the longitudinal direction of the main body 31 (a plane containing the center axis of the main body 31) be a plane f9, and let the angle formed between the plane f9 and the minor axis J31 at the central portion S4 be an inclination angle θ1, then the inclination angle θ1 is preferably an acute angle. With the inclination angle θ1 set to be an acute angle, an implant 9 (described later) can be disposed substantially in parallel to the urethra, so that the urethra can be supported more effectively. This effect will be described in detail later.

Note that the inclination angle θ1 is not particularly limited so long as it is an acute angle. In accordance with an exemplary embodiment, for example, the inclination angle θ1 is about 20° to 60°, more preferably 30° to 45°, and further preferably about 35° to 40°.

While it is preferable that the inclination angle θ1 satisfies the aforementioned numerical range over the whole region in the extending direction of the main body 31, the above-mentioned effect can be exhibited if the aforementioned numerical range is satisfied at least at the central portion S4 in the extending direction of the main body 31. Note that the "central portion S4" means a region including the part located between the urethra and the vagina at least in a state where a living body is punctured by the puncture member 3 (a state where the main body 31 is disposed inside the living body). In this exemplary embodiment, it can be also said that a central portion (the center and the vicinity on both sides of the same) between the anchors 81 and 82, in a state where the anchors 81 and 82 are in engagement with the puncture member 33 as will be described later, is the central portion S4.

Note that both end portions of the main body 31 may be provided with markers at parts which are located equidistantly from the central portion S4 and which protrude to the outside of a living body in a state where the main body 31 is disposed in the living body (the state shown in FIG. 22), which can help ensure that the position of the central portion S4 inside the living body can be confirmed by comparing the positions of both the markers.

Figure 10:
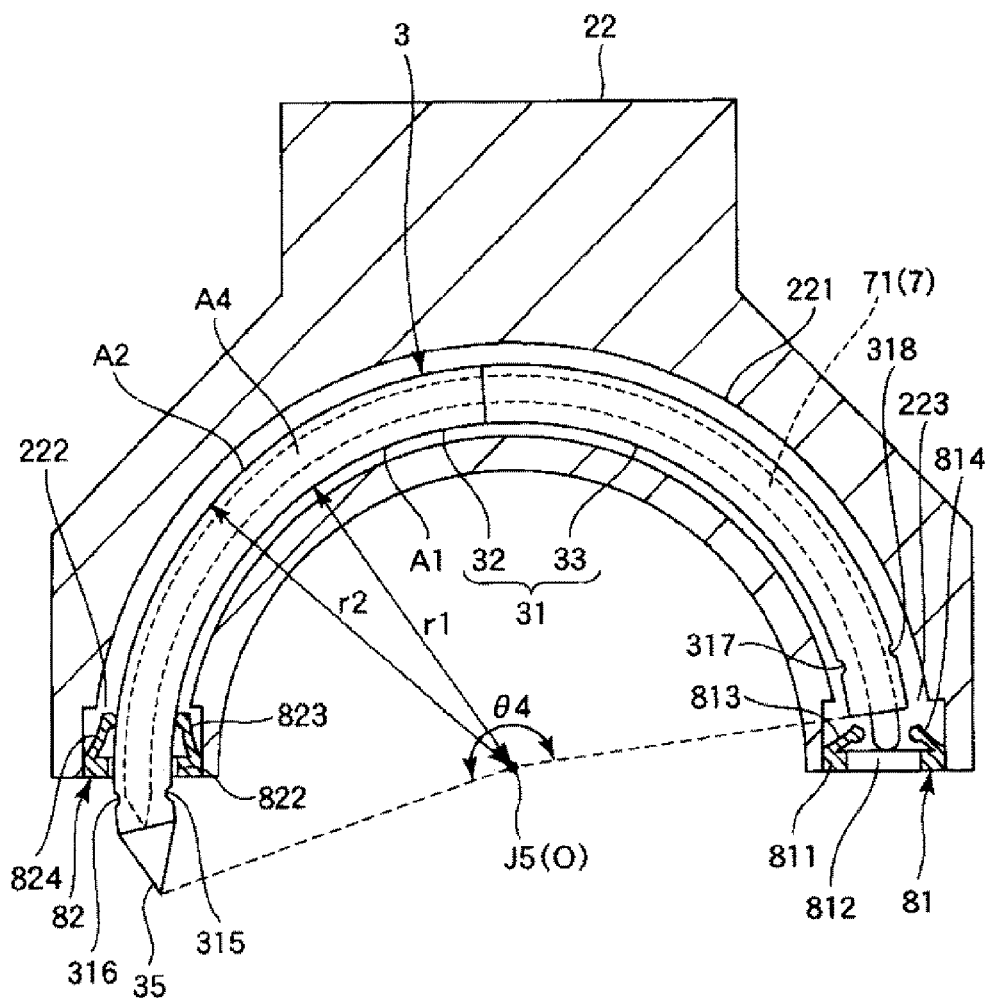
FIG. 10 is a sectional view showing a guide section of a frame possessed by the puncture device shown in FIG. 1.

The configuration of the main body 31 can be described in other words as follows. It can be also said that as shown in FIG. 4(b), the main body 31 is so formed that the major axis J32 is inclined against the center axis J5 of the circular arc and that the center axis J5 of the circular arc and an extension line J32' of the major axis J32 have an intersection P. In this case, the angle θ5 formed between the center axis J5 and the extension line J32' is equal to the inclination angle θ1. In still other words, it can be also said that as shown in FIG. 10, in plan view as viewed from the direction of the center axis J5 of the main body 31, the main body 31 has the inner circumferential portion A1 located at its inner circumferential edge and having a minimum radius of curvature r1 and the outer circumferential portion A2 located at its outer circumferential edge and having a maximum radius of curvature r2, and, as shown in FIG. 4(b), the inner circumferential portion A1 and the outer circumferential portion A2 are located to be spaced from each other in the direction of the center axis J5.

The main body 31 thus shaped is composed of two separable pieces so that it can be divided at an intermediate portion thereof. In accordance with an exemplary embodiment, the main body 31 is divided into a distal separable piece 32 and a proximal separable piece 33. The distal separable piece 32 and the proximal separable piece 33 are substantially the same in length, and the boundary between the two separable pieces is located in the central portion S4.

Figure 5:
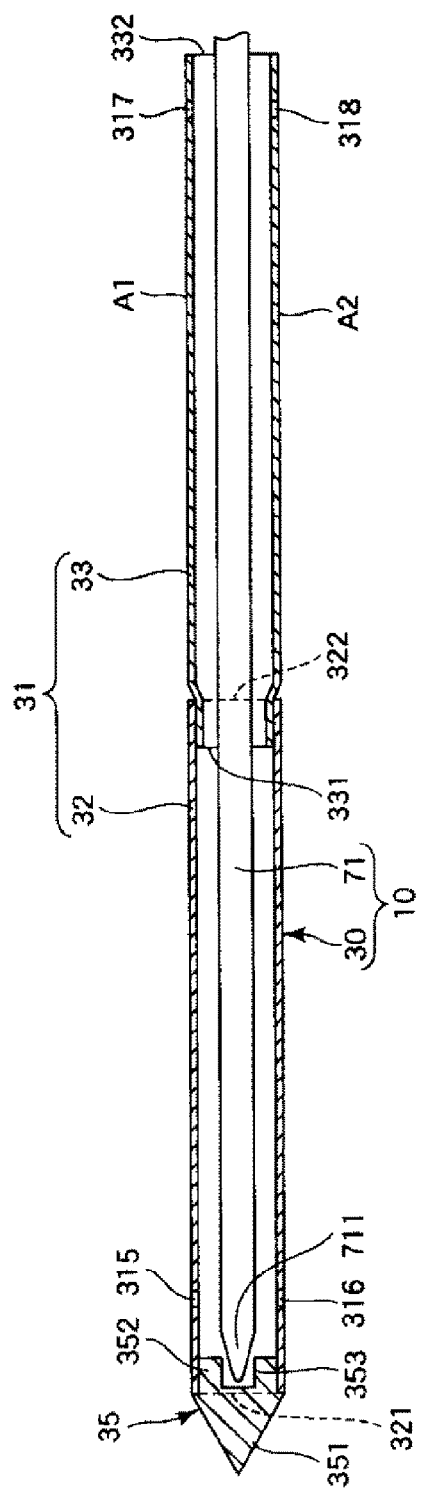
FIG. 5 is a sectional view of the puncture member shown in FIG. 4(a).

As shown in FIG. 5, the distal separable piece 32 is tubular in shape, and has a distal-side opening 321 and a proximal-side opening 322. In addition, the proximal separable piece 33 is tubular in shape, and has a distal-side opening 331 and a proximal-side opening 332. A distal portion of the proximal separable piece 33 is inserted in a proximal portion of the distal separable piece 32, whereby the distal separable piece 32 and the proximal separable piece 33 are connected with each other. With the proximal separable piece 33 thus inserted in the distal separable piece 32, a step which could be generated at the boundary between the separable pieces 32 and 33 is unlikely to be caught on the biological tissue, so that puncture of a living body by the puncture member 3 can be performed smoothly. Note that contrary to this embodiment, the distal separable piece 32 may be inserted in the proximal separable piece 33 to thereby connect the separable pieces 32 and 33 together.

The connected state in which these separable pieces 32 and 33 are connected together is maintained by the state maintaining mechanism 34. As shown in FIG. 6(a), the state maintaining mechanism 34 can include holes 342a, 342b and 342c; an endless string (interlock member) 341 inserted in and passed through the holes 342a, 342b and 342c; exposure holes (through-holes) 345 and 346 for exposure of the string 341; and a slit 347 interconnecting the exposure holes 345 and 346.

The hole 342a is provided in a proximal portion of the proximal separable piece 33 at a position near the inner circumferential portion A1 of the front surface A3. In accordance with an exemplary embodiment, the holes 342b and 342c are provided in a proximal portion of the distal separable piece 32, oppositely at positions which are in the front surface A3 and the back surface A4 and which are near the inner circumferential portion A1.

The string 341 is disposed inside the main body 31, while being exposed outside of the main body 31 between the holes 342b and 342c and between the hole 342a and the proximal-side opening 332. With the string 341 laid around in this manner, the connected state of the separable pieces 32 and 33 can be maintained assuredly. In addition, the degree of exposure of the string 341 outside of the main body 31 can be lowered, so that the string 341 is less liable to be caught on the biological tissue. In accordance with an exemplary embodiment, the overall length of the string 341 can be made as short as possible, while enabling the string 341 to be cut as will be described later. Therefore, the string 341 is less liable to be caught on the implant main body 91 at the time of inserting and passing the implant main body 91 into and through the main body 31. Further, since the holes 342a, 342b and 342c are disposed near the inner circumferential portion A1 as aforementioned, the string 341 is also disposed near the inner circumferential portion A1. Therefore, the string 341 is less likely to be caught on the implant main body 91 at the time of inserting the implant main body 91 into the main body 31.

The string 341 as above can be obtained, for example, by a method wherein a string having ends is prepared, one end of the string is inserted into the main body 31 via the proximal-side opening 332, is drawn out to the outside of the main body 31 through the hole 342b, is inserted into the main body 31 via the hole 342c, is drawn out to the outside of the main body 31 through the hole 342a, and, finally, is tied with the other end of the string in the vicinity of the proximal-side opening 332. It is to be noted, however, that the position of the knot is not limited.

Here, as shown in FIG. 6(c), the axis of the hole 342a is inclined so that the outside opening is located on the proximal side as compared with the inside opening. In accordance with an exemplary embodiment, as shown in FIG. 6(b), the axis of each of the holes 342b and 342c is inclined so that the outside opening is located on the distal side as compared with the inside opening, which can help ensure that each of the holes 342a, 342b and 342c can be extended along the path of the string 341, so that the string 341 is less liable to be caught on each of the holes 342a, 342b and 342c.

The exposure holes 345 and 346 are oppositely provided in the front surface A3 and the back surface A4 of the proximal portion of the proximal separable piece 33. The part where the exposure holes 345 and 346 are provided protrudes from a body surface in a state where the main body 31 is disposed inside a living body. In addition, the exposure holes 345 and 346 are located on the path of the string 341. Therefore, the string 341 is exposed outside of the main body 31 via the exposure holes 345 and 346. In accordance with an exemplary embodiment, these exposure holes 345 and 346 are interconnected by the slit 347 provided in the inner circumferential portion A1 along the circumferential direction of the main body 31.

In the state maintaining mechanism 34 as above, cutting the string 341 results in a state in which the distal separable piece 32 and the proximal separable piece 33 are separable from each other. This configuration can help enable the distal separable piece 32 and the proximal separable piece 33 to be put into a separable state through a simple operation. In addition, since the cutting of the string 341 is visible, it can be relatively easily confirmed that the distal separable piece 32 and the proximal separable piece 33 have been put into the separable state.

With the exposure holes 345 and 346 and the slit 347 provided as in this embodiment, the string 341 can be cut relatively easily. Referring to one example, scissors including a pair of blades (a first blade and a second blade) are prepared, the first blade is inserted into and passed through the exposure holes 345 and 346, and the string 341 is positioned between the pair of blades. Then, the scissors are put into a closing operation, whereby at least one of the first and second blades is passed through the slit 347, and the first and second blades come to overlap with each other, in which process the string 341 is cut. Thus, where the exposure holes 345 and 346 and the slit 347 are provided, the string 341 can be cut relatively easily.

Figure 7A:
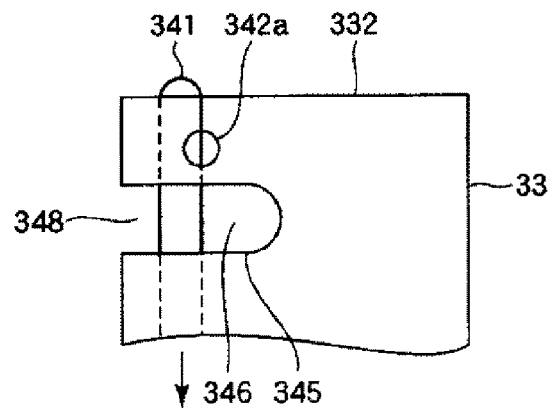
Figure 7B:
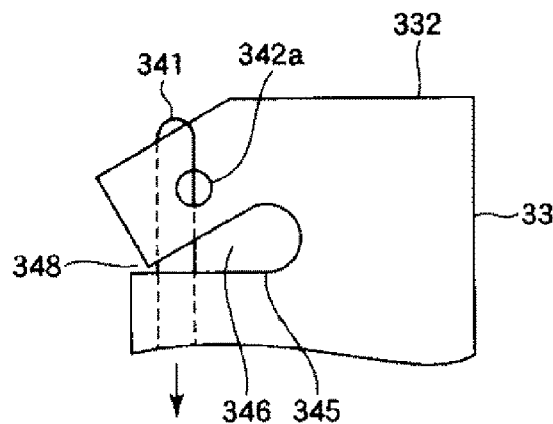
Figure 7C:
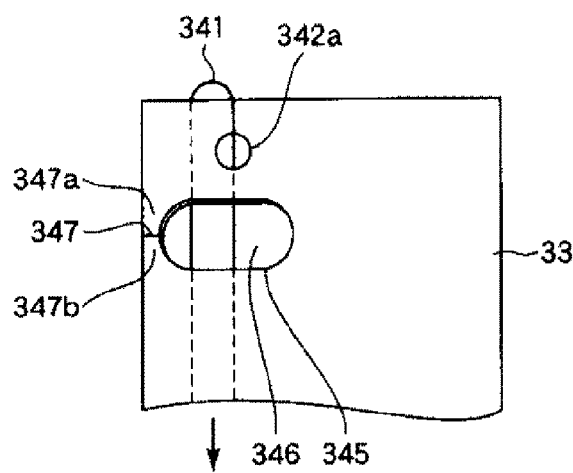

As above-mentioned, in this embodiment, the slit 347 is provided, and the slit 347 is used as a path along which the blade passes, which can help prevent the main body 31 from being deformed under a tension on the string 341. In accordance with an exemplary embodiment, as shown in FIG. 7(a), the path along which the blade is passed may be composed of a hole 348 instead of the slit 347. In this case, however, depending on the hardness of the main body 31 or the like there may arise a situation where as shown in FIG. 7(b), the hole 348 may be crushed through buckling under the tension on the string 341, resulting in deformation of the main body 31. In the case of the slit 347, for example, since parts 347a and 347b on both sides of the slit 347 abut on and are pressed against each other, as shown in FIG. 7(c), such a deformation as above-mentioned would not occur, so that the main body 31 is prevented from deformation.

In accordance with an exemplary embodiment, as shown in FIG. 5, the main body 31 is provided in a distal portion thereof with a pair of engaging holes 315 and 316 for engagement with the anchor 81. In accordance with an exemplary embodiment, the main body 31 is provided in a proximal portion thereof with a pair of engaging holes 317 and 318 for engagement with the anchor 82. Out of the four engaging holes, the engaging holes 315 and 317 are provided in the inner circumferential portion A1, whereas the engaging holes 316 and 318 are provided in the outer circumferential portion A2.

As aforementioned, the main body 31 is flat shaped and is less liable to be crushed in the major axis direction, so that the spacing between the inner circumferential portion A1 and the outer circumferential portion A2 is unlikely to vary. In addition, the inner circumferential portion A1 and the outer circumferential portion A3 are larger in curvature and, hence, less susceptible to deformation, as compared with the front surface A3 and the back surface A4. With the engaging holes 315 and 317 provided in the inner circumferential portion A1 and with the engaging holes 316 and 318 provided in the outer circumferential portion A2, therefore, the engagement between the anchors 81 and 82 and the main body 31 is unlikely to be released.

In addition, the spacing between the engaging holes 315 and 316 and the central portion S4 and the spacing between the engaging holes 317 and 318 and the central portion S4 are approximately equal, which can help ensure that the anchors 81 and 82 serve as markers, whereby the position of the central portion S4 of the main body 31 inside a living body can be easily grasped.

The main body 31 as above is provided at the distal end thereof with the needle body 35. As depicted in FIG. 5, the needle body 35 can include a needle tip 351, which is tapered off, and a proximal section 352 provided on the proximal side of the needle tip 351. The proximal section 352 is inserted in the main body 31, whereby the needle body 35 is detachably retained on the main body 31. Note that the proximal section 352 is fitted in the main body 31 with such a force that the needle body 35 can be prevented from being unintentionally detached from the main body 31. Note that the needle body 35 may be configured to be integral with the main body 31.

The proximal section 352 is provided with an engaging section 353 for engagement with the distal portion 711 of the insertion section 71. The engaging section 353 can include a recess, and, in an inserted state where the puncture member 3 is inserted in the insertion section 71, the distal portion 711 is located inside the engaging section 353. With the engaging section 353 provided, displacement of the needle body 35 relative to the insertion section 71 is restrained, and puncture of a living body by the puncture member 3 can be performed relatively smoothly.

The puncture member 3 has thus been described above. The center angle θ4 of the puncture member 3 is not particularly limited, and is appropriately set according to various conditions. As will be described later, the center angle θ4 is so set that the needle body 35 can enter a patient's body via an inguinal region on one side of the patient, pass between the urethra and the vagina, and exit the body via an inguinal region on the other side. In accordance with an exemplary embodiment, the center angle θ4 is preferably 150° to 270°, more preferably 170° to 250°, and further preferably 190° to 230°.

The materials constituting the main body 31 and the needle body 35 are preferably rigid materials such as to maintain the shape of the puncture member 3 and the internal space in a state where the puncture member 3 is inserted in a living body. Examples of such rigid materials applicable here include, for example, various resin materials such as polyethylene, polyimides, polyamides, polyester elastomers, polypropylene, and various metallic materials such as stainless steel, aluminum or aluminum alloys, titanium or titanium alloys. Note that the main body 31 and the needle body 35 may not necessarily be configured by adopting rigid materials, but may be configured by adopting other materials than rigid materials; in the latter case, the wall may be reinforced with a reinforcement member. For example, a braiding with high strength may be embedded in the wall, whereby the shape and the internal space can be maintained in the state where the puncture member 3 is inserted in a living body. Another example of the reinforcement member is a spiral body, which is embedded in the wall of the main body 31, whereby flexibility can be ensured while the internal space is retained to such an extent that an inserted article can be slid therein.

The main body 31 is preferably light-transmitting so that the inside thereof can be visually checked externally. This makes it possible, for example, to check whether the distal portion 711 of the insertion section 71 inserted to the inside is in engagement with the engaging section 353, whether the string 341 has not been cut, and so on.

The aforementioned puncture member 3 (main body 31) and the insertion section 71 which is inserted into the main body 31 constitute a medical tube assembly 10; use of the puncture device 1 is started with these members being in the state of the medical tube assembly 10.

Note that the number and layout of the holes (342a, 342b and 342c) through which to pass the string 341 are not particularly limited insofar as the connected state of the distal separable piece 32 and the proximal separable piece 33 can be maintained by the string 341. The string 341 may not necessarily be endless, but may have ends, for example, one end and the other end. For example, a string having ends may be prepared, one end of the string may be passed through the hole 342a and the proximal-side opening 332 to form a loop, and the other end may be passed through the holes 342b and 342c to form a loop. The string 341 can include cords, belts and the like which can be used similarly to the string 341.

Figure 8A:
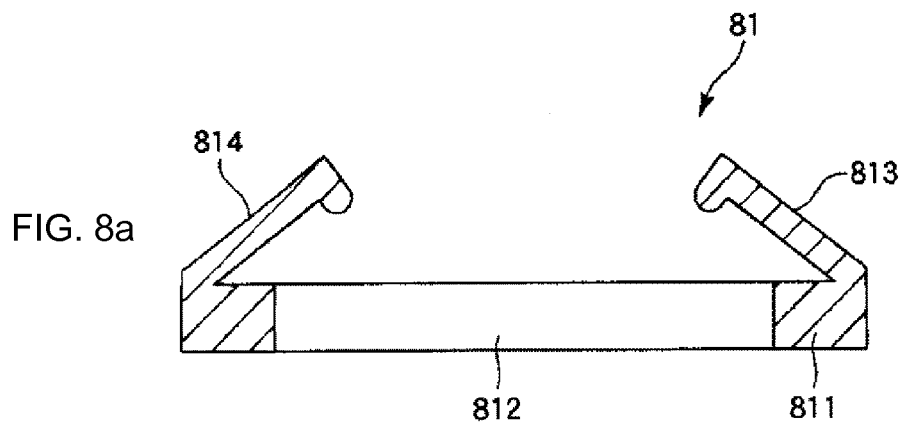
Figure 8B:
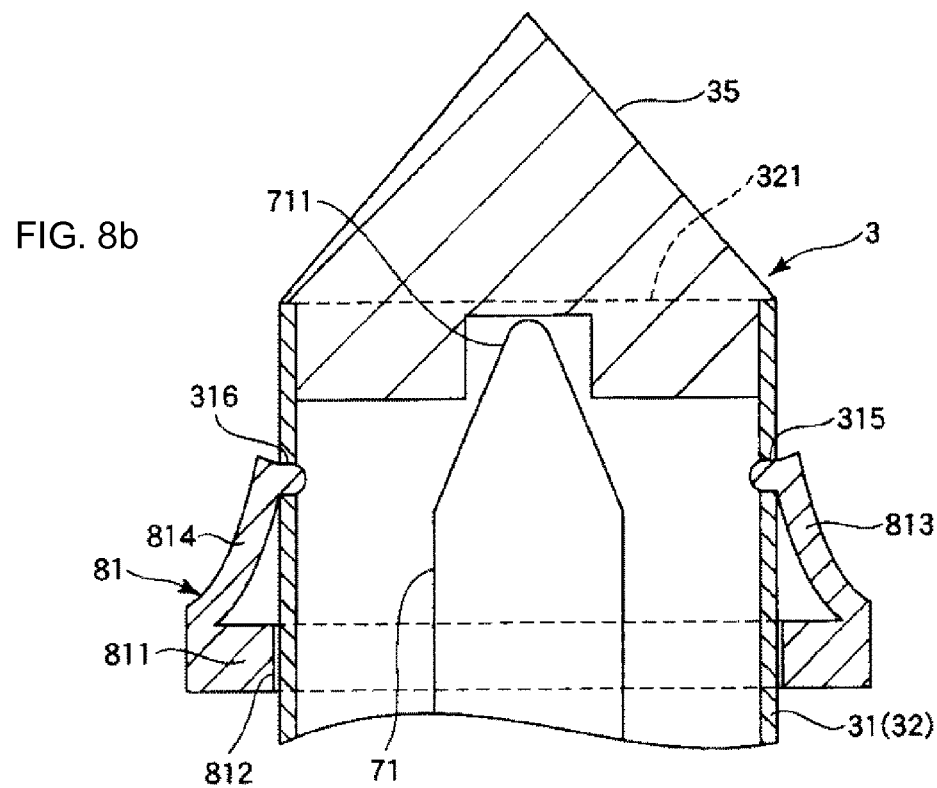

As shown in FIG. 8(a), the anchor (second anchor) 81 can include a base section 811 having an insertion hole 812 in and through which the main body 31 is inserted and passed, and a pair of claw sections 813 and 814 projecting from the base section 811 and engaging with the pair of engaging holes 315 and 316. The cross-sectional shape of the insertion hole 812 corresponds to the cross-sectional shape of the main body 31. In a state where the puncture member 3 is inserted in and passed through the insertion hole 812, therefore, rotation of the anchor 81 relative to the puncture member 3 is restrained, and the positional relation between these members is maintained appropriately. When the puncture member 3 is inserted into the insertion hole 812 and the puncture member 3 is pushed forward in relation to the anchor 81, the claw sections 813 and 814 are engaged with the engaging holes 315 and 316, as shown in FIG. 8(b). As a result, the anchor 81 is engaged with the distal separable piece 32. In the engaged state, the base section 811 is located on the proximal side as compared with the claw sections 813 and 814. As aforementioned, rotation of the anchor 81 relative to the puncture member 3 is restrained in the state where the puncture member 3 is inserted in and passed through the insertion hole 812, and, accordingly, the engagement between the claw sections 813 and 814 and the engaging holes 315 and 316 can be developed assuredly.

Figure 9A:
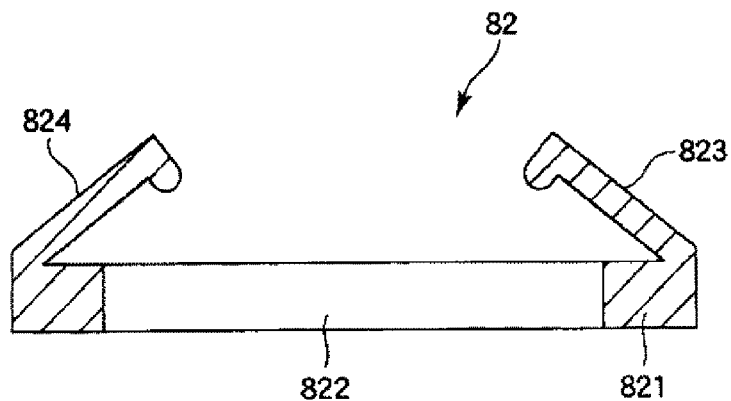
Figure 9B:
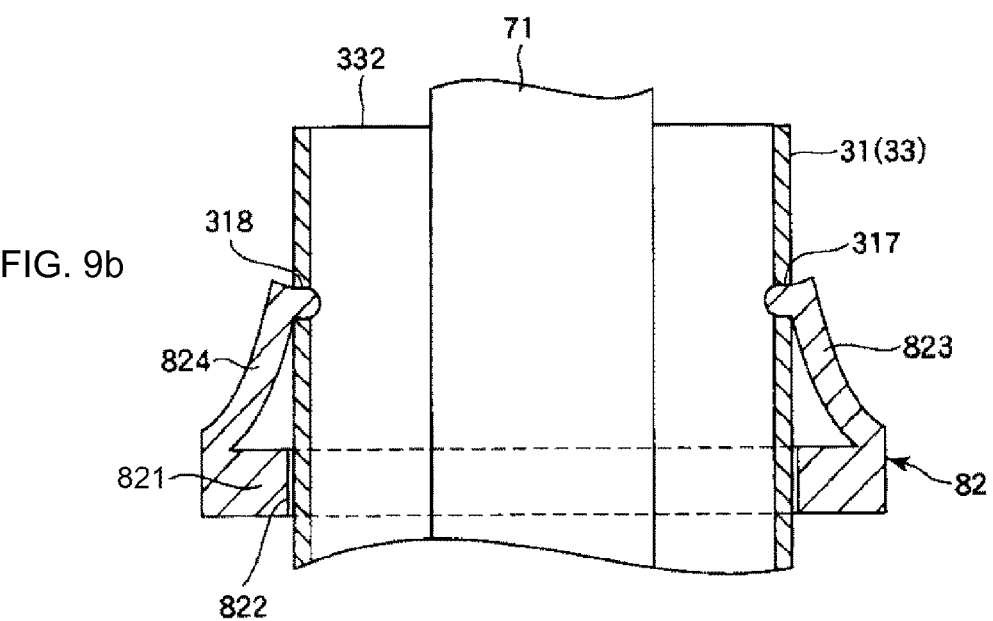

Similarly, as shown in FIG. 9(a), the anchor (first anchor) 82 can include a base section 821 having an insertion hole 822 in and through which the main body 31 is inserted and passed, and a pair of claw sections 823 and 824 projecting from the base section 821 and engaging with the pair of engaging holes 317 and 318. The cross-sectional shape of the insertion hole 822 corresponds to the cross-sectional shape of the main body 31. In a state where the puncture member 3 is inserted in and passed through the insertion hole 822, therefore, rotation of the anchor 82 relative to the puncture member 3 is restrained, and the positional relation between these members is maintained appropriately. When the puncture member 3 is inserted into the insertion hole 812 and the puncture member 3 is pushed forward in relation to the anchor 82, therefore, the claw sections 823 and 824 are engaged with the engaging holes 317 and 318, as depicted in FIG. 9(b). As a result, the anchor 82 is engaged with the proximal separable piece 33. As aforementioned, rotation of the anchor 82 relative to the puncture member 3 is restrained in the state where the puncture member 3 is inserted in and passed through the insertion hole 822, and, accordingly, engagement between the claw sections 823 and 824 and the engaging holes 317 and 318 can be developed relatively assuredly.

The materials constituting the anchors 81 and 82 are not particularly limited; for example, various resin materials can be used.

The frame 2 retains the operating member 7 with the puncture member 3 mounted thereto so that the operating member 7 is turnable, and fixes the insertion tool 6 and the anchors 81 and 82 in an attachable and detachable manner. The frame 2 has a function of determining a puncture path of the needle body 35 when the puncture member 3 punctures the biological tissue. In accordance with an exemplary embodiment, the frame 2 can determine the positional relations of the puncture member 3, the urethral-insertion member 4 and the vaginal-insertion member 5 so that the needle body 35 passes between the urethral-insertion member 4 and the vaginal-insertion member 5 without colliding against any of these insertion members when the puncture member 3 punctures the biological tissue.

As shown in FIGS. 1 and 2, the frame 2 can include a bearing section 21 for bearing the shaft section 73 of the operating member 7; a guide section (retaining section) 22 for guiding the puncture member 3 and retaining the first and second anchors 82 and 81 in an attachable and detachable manner; an interlock section 23 interlocking the bearing section 21 and the guide section 22; and a fixing section 24 to which the insertion tool 6 is fixed.

The bearing section 21 is located on the proximal side of the puncture device 1, and extends in a direction substantially orthogonal to the axis J1. The bearing section 21 is formed with a through-hole 211 on the axis J1, and the shaft section 73 is turnably inserted in the through-hole 211. As a result, the operating member 7 is supported on the frame 2 so as to be turnable about the axis J1.

Figure 11:
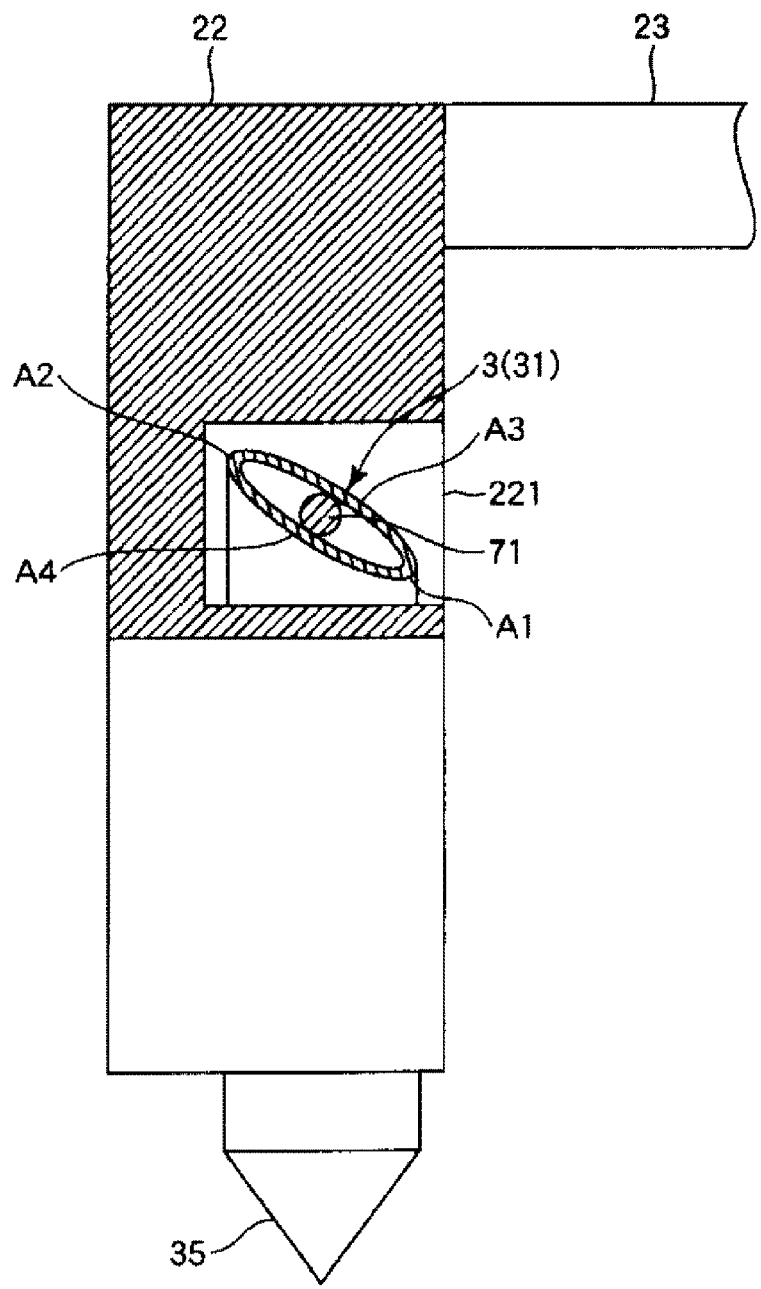
FIG. 11 is a sectional view showing the guide section of the frame possessed by the puncture device shown in FIG. 1.

The guide section 22 is located on the distal side of the puncture device 1, and is disposed opposite to the bearing section 21. As shown in FIG. 10, the guide section 22 is formed therein with a roughly C-shaped guide groove 221 for accommodating the puncture member 3 and guiding the puncture member 3. In accordance with an exemplary embodiment, as shown in FIG. 11, in a state of being disposed within the guide groove 221, the puncture member 3 has its back surface A4 located on the distal side and has its front surface A3 located on the proximal side.

In addition, the guide section 22 retains the anchors 81 and 82 in an attachable and detachable manner. The anchor 82 is retained to face the distal-side opening 222 so that the insertion hole 822 and the guide groove 221 are continuous with each other. The anchor 81 is retained to face the proximal-side opening 223 of the guide groove 221 so that the insertion hole 812 and the guide groove 221 are continuous with each other.

Figure 12:
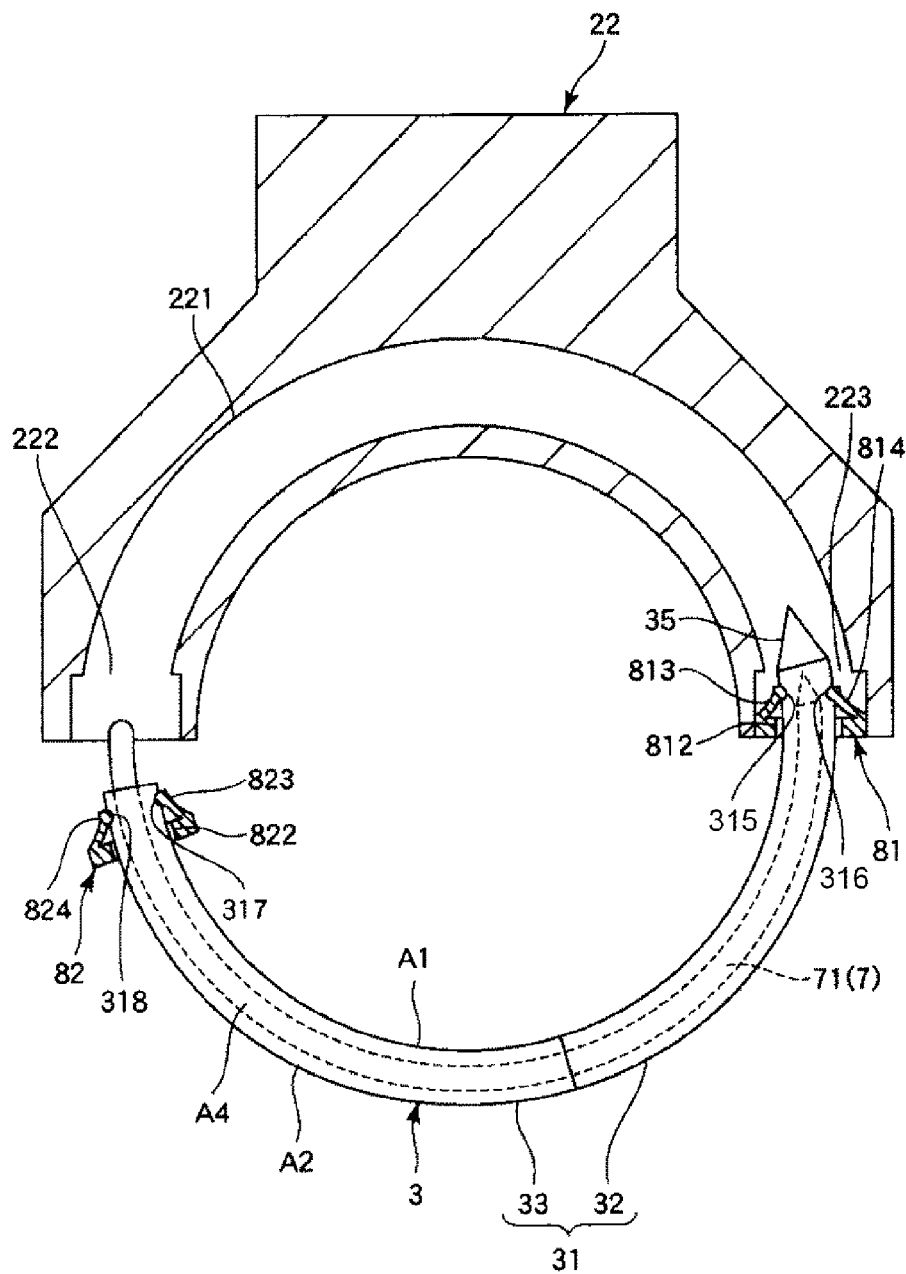
FIG. 12 is a sectional view showing the guide section of the frame possessed by the puncture device shown in FIG. 1.
Figure 13:
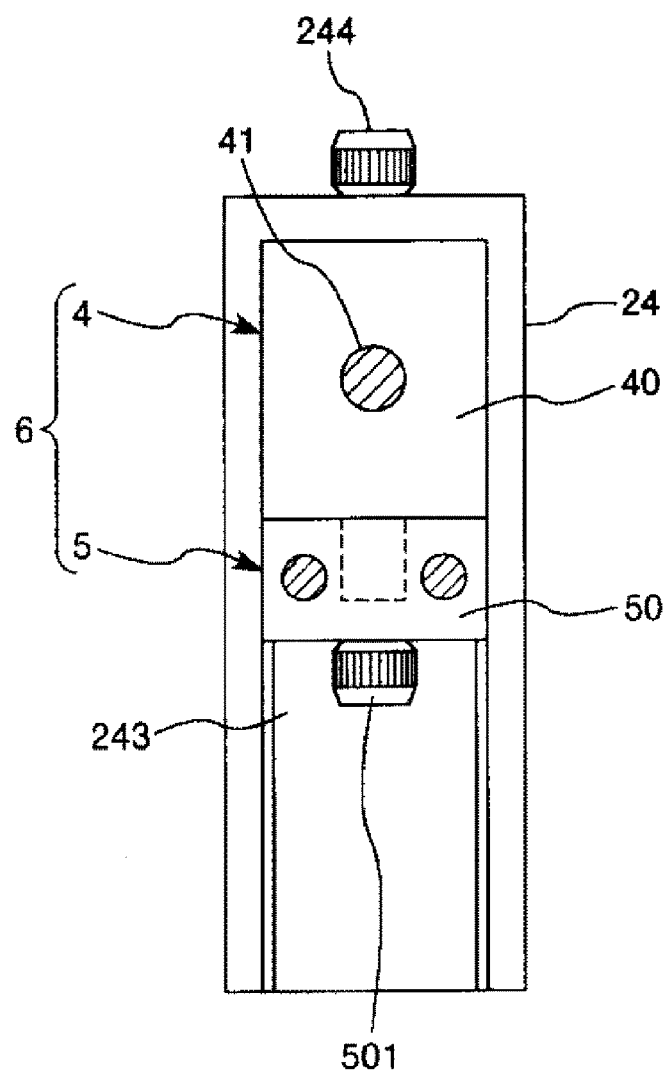
FIG. 13 is a plan view showing a fixing section of the frame possessed by the puncture device shown in FIG. 1.

In the initial state, the main body 31 is inserted in and passed through the insertion hole 822 of the anchor 82, and the needle body 35 is protruding from the guide section 22. When the operating member 7 is rotated, the puncture member 3 gradually protrudes from the guide section 22, and, finally, the needle body 35 enters into the guide section 22 via the proximal-side opening 223, as shown in FIG. 12. In this process, on the distal side of the puncture member 3, the puncture member 3 is passed through the insertion hole 812 of the anchor 81, and the claw sections 813 and 814 are engaged with the engaging holes 315 and 316. In accordance with an exemplary embodiment, on the proximal side of the puncture member 3, the claw sections 823 and 824 are engaged with the engaging holes 317 and 318. As a result, the anchors 81 and 82 are engaged with the puncture member 3.

The interlock section 23 interlocks the bearing section 21 and the guide section 22. In accordance with an exemplary embodiment, the interlock section 23 has a rod-like shape extending substantially in parallel to the axis J1. The interlock section 23 functions also as a grip section, and an operator can use the puncture device 1 by gripping the interlock section 23.

The fixing section 24 is disposed opposite to the interlock section 23, with the axis J1 interposed therebetween. The fixing section 24 is provided with a recess 243 in which to fit a support section 60 (described later) of the insertion tool 6, and a male screw 244. With the support section 60 fitted into the recess 243 and with the male screw 244 fastened into a female screw (not illustrated) of the support section 60, the insertion tool 6 can be fixed to the fixing section 24.

Figure 14:
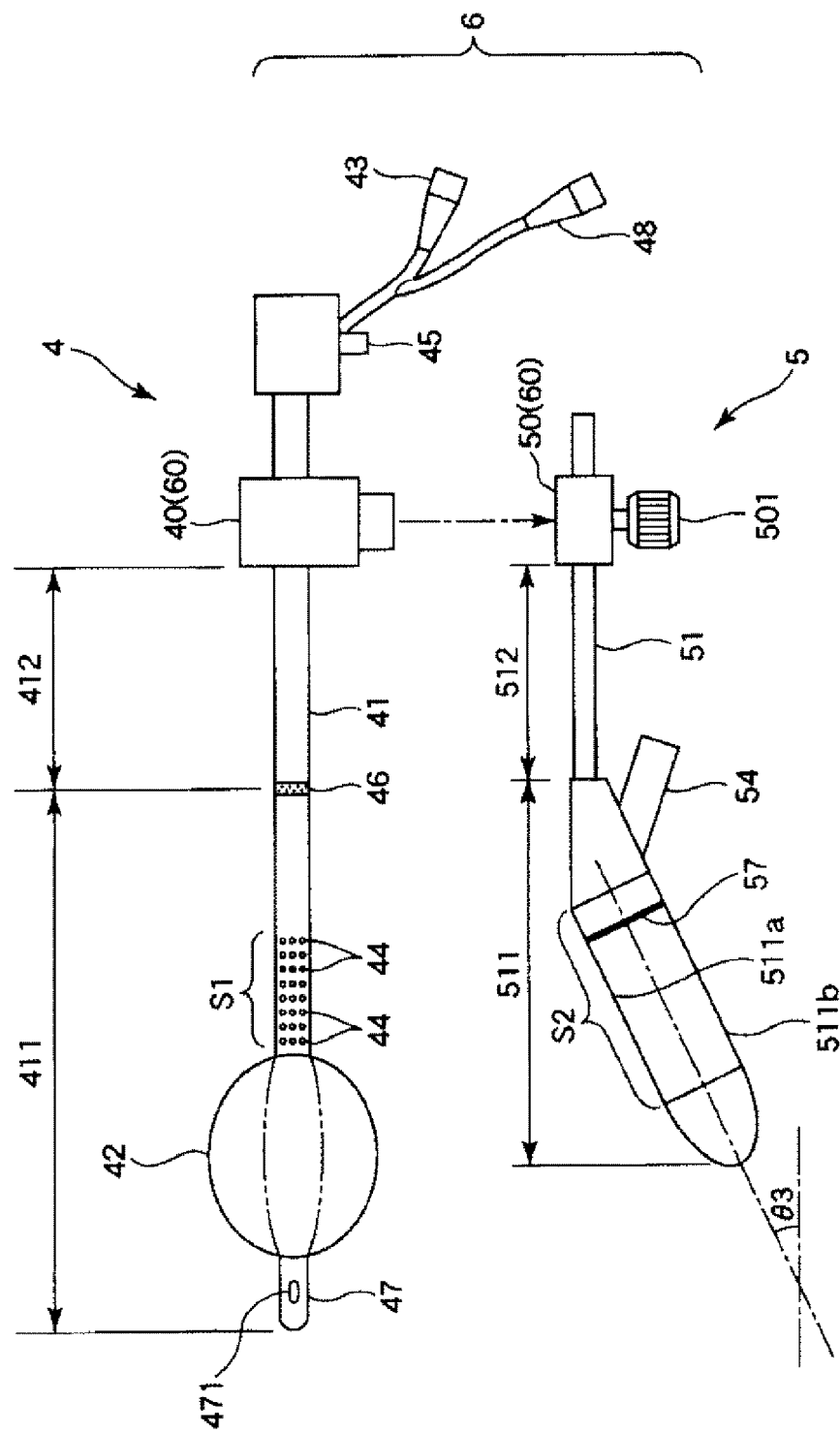
FIG. 14 is a side view of an insertion tool possessed by the puncture device shown in FIG. 1.

As illustrated in FIGS. 1 and 14, the insertion tool 6 can include a urethral-insertion section (second insertion section) 41 to be inserted into a urethra; a vaginal-insertion section (first insertion section) 51 to be inserted into a vagina; and the support section 60 supporting the urethral-insertion section 41 and the vaginal-insertion section 51. As aforementioned, the insertion tool 6 can include the urethral-insertion member 4 and the vaginal-insertion member 5, wherein the urethral-insertion member 4 has the urethral-insertion section 41, and the vaginal-insertion member 5 has the vaginal-insertion section 51. The support section 60 can include a support section 40 which is possessed by the urethral-insertion member 4 and which supports the urethral-insertion section 41; and a support section 50 which is possessed by the vaginal-insertion member 5 and which supports the vaginal-insertion section 51. In the insertion tool 6, the urethral-insertion member 4 and the vaginal-insertion member 5 can be attached to and detached from each other through the support sections 40 and 50. The urethral-insertion member 4 and the vaginal-insertion member 5 will be sequentially described below.

The urethral-insertion member 4 can include the urethral-insertion section 41 which is elongated and which, from its distal end to its intermediate portion, is to be inserted into the urethra, and the support section 40 supporting the urethral-insertion section 41. Note that in the following, for convenience of explanation, the part located inside the urethra (inclusive of the bladder) in the mounted state will be referred to also as the "insertion section 411," whereas the part exposed from the urethral orifice to the outside of the body in the mounted state will be referred to also as the "non-insertion section 412."

The urethral-insertion section 41 has a straight tubular shape with the distal end rounded. The insertion section 411 is provided at a distal portion thereof with an expandable and contractible balloon 42, and a urine drain section 47. The balloon 42 functions as a restricting section which restricts the position in the axial direction of the urethral-insertion member 4 within the urethra. In accordance with an exemplary embodiment, at the time of using the puncture device 1, the balloon 42 is expanded after inserted into a patient's bladder. Then, the expanded balloon 42 is caught on a bladder neck, whereby the position of the urethral-insertion member 4 relative to the bladder and the urethra is fixed. In accordance with an exemplary embodiment, the urine drain section 47 is used for draining urine present in the bladder.

The balloon 42 is connected to a balloon port 43 provided at a proximal portion of the urethral-insertion section 41, through the inside of the urethral-insertion section 41. A balloon expanding device such as a syringe can be connected to the balloon port 43. The balloon 42 is expanded when a working fluid (a liquid such as physiological saline, or a gas or the like) is supplied from the balloon expanding device into the balloon 42. On the contrary, the balloon 42 is contracted when the working fluid is drawn out of the balloon 42 by the balloon expanding device. Note that in FIG. 14, the contracted state of the balloon 42 is indicated by alternate long and two short dashes line, and the expanded state of the balloon 42 is indicated by solid line.

In accordance with an exemplary embodiment, the urine drain section 47 is provided with a drain hole 471 through which the inside and the outside of the urine drain section 47 communicate with each other. The urine drain section 47 is connected to a urine drain port 48 provided at a proximal portion of the urethral-insertion section 41, through the inside of the urethral-insertion section 41. Therefore, urine introduced via the drain hole 471 can be drained via the urine drain port 48.

The balloon 42 and the urine drain section 47 can be configured, for example, by a double lumen.

The insertion section 411 is formed at an intermediate portion thereof with a plurality of suction holes 44. In accordance with an exemplary embodiment, the plurality of suction holes 44 are disposed over the whole circumferential range of the urethral-insertion section 41. Each of the suction holes 44 is connected to a suction port 45 provided at a proximal portion of the urethral-insertion section 41, through the urethral-insertion section 41. A suction device such as a pump can be connected to the suction port 45. When the suction device is operated in a state where the urethral-insertion section 41 is inserted in the urethra, a urethral wall can be secured by suction onto the urethral-insertion section 41. When in this condition the urethral-insertion section 41 is pushed in toward the distal side (into the living body), the urethra is also pushed in as a result, whereby, for example, the bladder can be shifted to such a position as not to overlap with a puncture path for the puncture member 3, and thereby the puncture path can be secured for the puncture member 3. Accordingly, puncture by the puncture member 3 can be performed relatively accurately and safely. Note that the number of the suction holes 44 is not particularly limited; for example, only one suction hole may be provided. In accordance with an exemplary embodiment, the layout of the suction holes 44 is not specifically restricted; for example, the suction holes 44 may be formed in only part in the circumferential direction of the urethral-insertion section 41.

At the boundary between the insertion section 411 and the non-insertion section 412, there is provided a marker 46 for confirming the depth of insertion of the urethral-insertion section 41 into the urethra. The marker 46 is located at the urethral orifice when the urethral-insertion section 41 is inserted in the urethra and the balloon 42 is located inside the bladder. As a result, the depth of insertion of the insertion section 411 into the urethra can be easily confirmed. It is sufficient for the marker 46 to be visibly checkable externally; thus, the marker 46 may be configured, for example, as a colored part, a rugged part or the like. Note that graduations indicative of the distance from the distal end of the urethral-insertion section 41 may be provided in place of the marker 46.

The length of the insertion section 411 is not particularly limited, and may be appropriately set according to the length of the patient's urethra, the shape of the patient's bladder, etc. In view of that the length of a female urethra is generally about 30 to 50 mm, it is preferred that the length of the insertion section 411 is about 50 to 100 mm.

The length of the non-insertion section 412 (the spacing between the urethral orifice and the support section 40) is not specifically restricted, and is preferably not more than about 100 mm, more preferably in the range of about 20 to 50 mm. By this, the non-insertion section 412 can be made to have a suitable length, and operability is enhanced. If the length of the non-insertion section 412 exceeds the above-mentioned upper limit, there may arise, depending on the configuration of the frame 2 or the like, a situation in which the center of gravity of the puncture device 1 is largely spaced from the patient and, accordingly, the stability of the puncture device 1 in the mounted state is lowered.

The material constituting the urethral-insertion member 4 is not particularly limited. For example, various metallic materials such as stainless steel, aluminum or aluminum alloys, titanium or titanium alloys, etc. and various resin materials can be used.

Here, for example, the inclination angle $\theta 2$ of the plane f9 (plane f1) against the plane f2 orthogonal to the axis J2 of the urethral-insertion section 41 is preferably about 20° to 60°, more preferably about 30° to 45°, and further preferably about 35° to 40°. In accordance with an exemplary embodiment, the main body 31 is preferably so set indwelling in a living body that the angle formed between the plane f9 and the plane orthogonal to the axis of the urethra is about 20° to 60°, more preferably so set indwelling in the living body that the angle is about 30° to 45°, and further preferably so set indwelling in the living body that the angle if about 35° to 40°, which can help ensure that puncture by the puncture member 3 can be performed easily, and the puncture distance in puncture by the puncture member 3 can be made shorter.

Figure 15A:
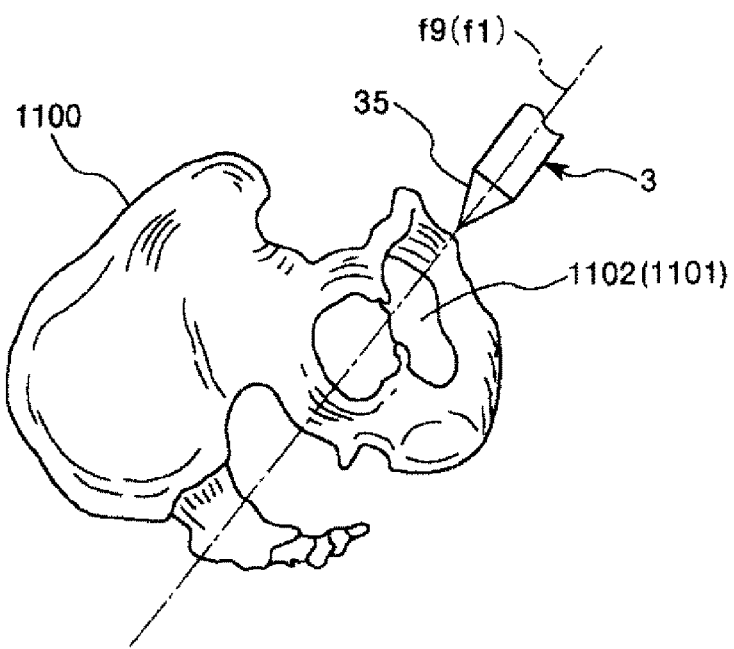
Figure 15B:
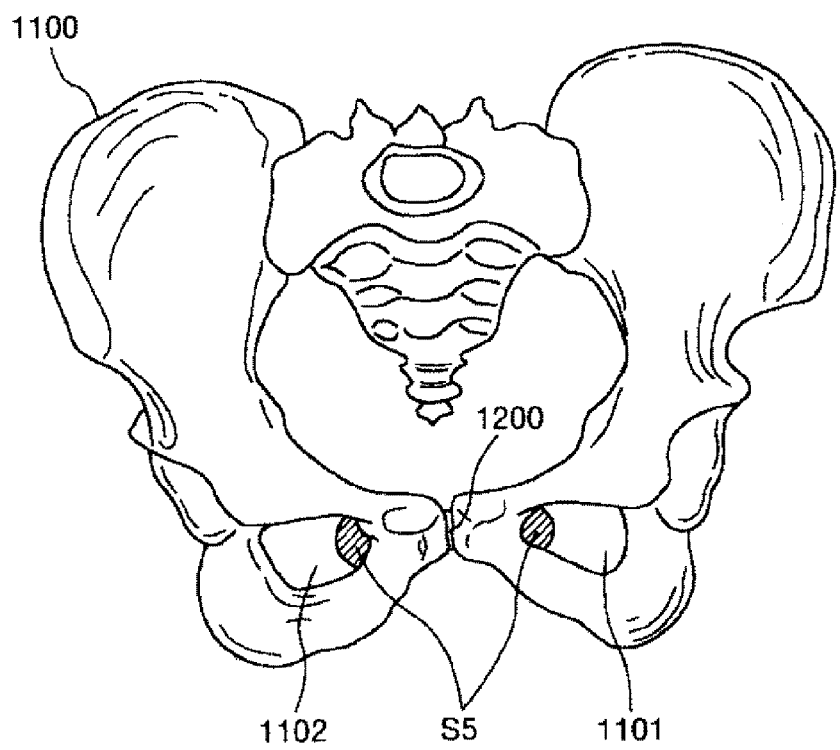

Describing more specifically, with the inclination angle $\theta 2$ set within the above-mentioned range, the puncture member 3 can capture left and right obturator foramens 1101 and 1102 of a pelvis 1100 wider on a planar basis, as depicted in FIG. 15(*a*), and a wide puncture space for the puncture member 3 can be secured. In accordance with an exemplary embodiment, in a state where a patient is set in a predetermined position (lithotomy position), the puncture member 3 can be made to puncture in a direction comparatively nearer to a perpendicular direction relative to the obturator foramens 1101 and 1102. Therefore, the puncture by the puncture member 3 can be carried out relatively easily. In addition, where the puncture member 3 is made to puncture in a direction comparatively nearer to the perpendicular direction relative to the obturator foramens 1101 and 1102, the needle body 35 of the puncture member 3 passes a shallow portion of the tissue, so that the needle body 35 of the puncture member 3 can pass between the left and right obturator foramens 1101 and 1102 while taking a shorter course. Therefore, as shown in FIG. 15(*b*), the puncture member 3 can be made to pass those zones in the obturator foramens 1101 and 1102 which are near a pubic symphysis 1200, preferably, safety zones S5. Since the safety zones S5 are parts where there are few nerves and blood vessels which should be prevented from being damaged, the puncture can be performed by the puncture member 3 relatively safely. Accordingly, a less invasive procedure is realized, and the burden on the patient can be reduced. Thus, with the inclination angle $\theta 2$ set within the above-mentioned range, the puncture of the patient by the puncture member 3 can be performed more suitably. In addition, the puncture at the aforementioned angle makes it easier to aim at the tissue between a middle-part urethra (which refers to a middle part in the longitudinal direction of the urethra) and the vagina. The position between the middle-part urethra and the vagina is a position suitable as a part where to perform treatment of urinary incontinence by embedding the implant 9.

In accordance with an exemplary embodiment, where the inclination angle $\theta 2$ is below the above-mentioned lower limit or above the above-mentioned upper limit, there may arise, depending on individual differences concerning the patient or the posture of the patient during the procedure or the like, a situation where the puncture member 3 cannot capture the obturator foramens 1101 and 1102 wide on a planar basis or where the puncture path cannot be made sufficiently short.

More preferably, for example, the puncture is conducted in a state where the urethra or the vagina or both the urethra and the vagina are positionally shifted in the manner of being pushed in toward the inner side of the body, whereby a region between the middle-part urethra and the vagina can be punctured relatively easily. The method for pushing in either one of the urethra and the vagina toward the inner side of the body can, for example, by a method wherein the urethral-insertion member 4 and/or the vaginal-insertion member 5 is inserted into a suitable position, then, in this condition, the urethra and/or the vagina is attracted by suction by the suction holes 44 and 59 (described later) provided in these insertion members, and thereafter the urethral-insertion member 4 and/or the vaginal-insertion member 5 is moved further toward the inner side of the body along the axis thereof to a predetermined position. Where the puncture is conducted by setting the main body 31 perpendicularly relative to the left and right obturator foramens 1101 and 1102 of the pelvis in the state where at least one of the urethra and the vagina has thus been positionally shifted in the manner of being pushed in toward the inner side of the body, a passage can be formed in a position suitable for indwelling of the implant 9.

It can be preferable to form the passage by adopting a setting such that the trajectory of the main body 31 passes the safety zones S5 in the left and right obturator foramens 1101 and 1102 of the pelvis, shifting at least one of the urethra and the vagina toward the inner side of the body so that the trajectory is positioned between the middle-part urethra and the vagina, and performing the puncture by the main body 31 along the trajectory.

As shown in FIGS. 1 and 14, the vaginal-insertion member 5 can include the vaginal-insertion section (first insertion section) 51 which is elongated and which, from its distal end to its intermediate portion, is to be inserted in the vagina; and the support section 50 which supports the vaginal-insertion section 51. Note that in the following, for convenience of explanation, the part located inside the vagina in the mounted state will be referred to also as the "insertion section 511," whereas the part which is exposed from the vaginal orifice to the outside of the body in the mounted state and which ranges to the support section 50 will be referred to also as the "non-insertion section 512."

The insertion section 511 is elongated in shape. The insertion section 511 extends while being inclined against the insertion section 411 so as to be spaced away from the insertion section 411 on the distal side. With the insertion section 511 inclined against the insertion section 411, the positional relation between the insertion sections 411 and 511 can be made closer to the positional relation between the urethra and the vagina, as compared with the case where the insertion section 511 is not inclined. Therefore, in the mounted state, the puncture device 1 can be held onto the patient more stably, and the burden on the patient can be alleviated. The inclination angle θ3 of the insertion section 511 against the insertion angle 411 is not particularly limited; for example, the inclination angle θ3 is preferably about 0° to 45°, more preferably about 0° to 30°, which helps enable the above-mentioned effects to be exhibited. In accordance with an exemplary embodiment, if the inclination angle θ3 is below the above-mentioned lower limit or above the above-mentioned upper limit, there may arise, depending on individual differences concerning the patient or the posture of the patient during the procedure, a situation in which the vagina or the urethra is unnaturally deformed in the mounted state, and the puncture device 1 is not held stably.

Figure 16:
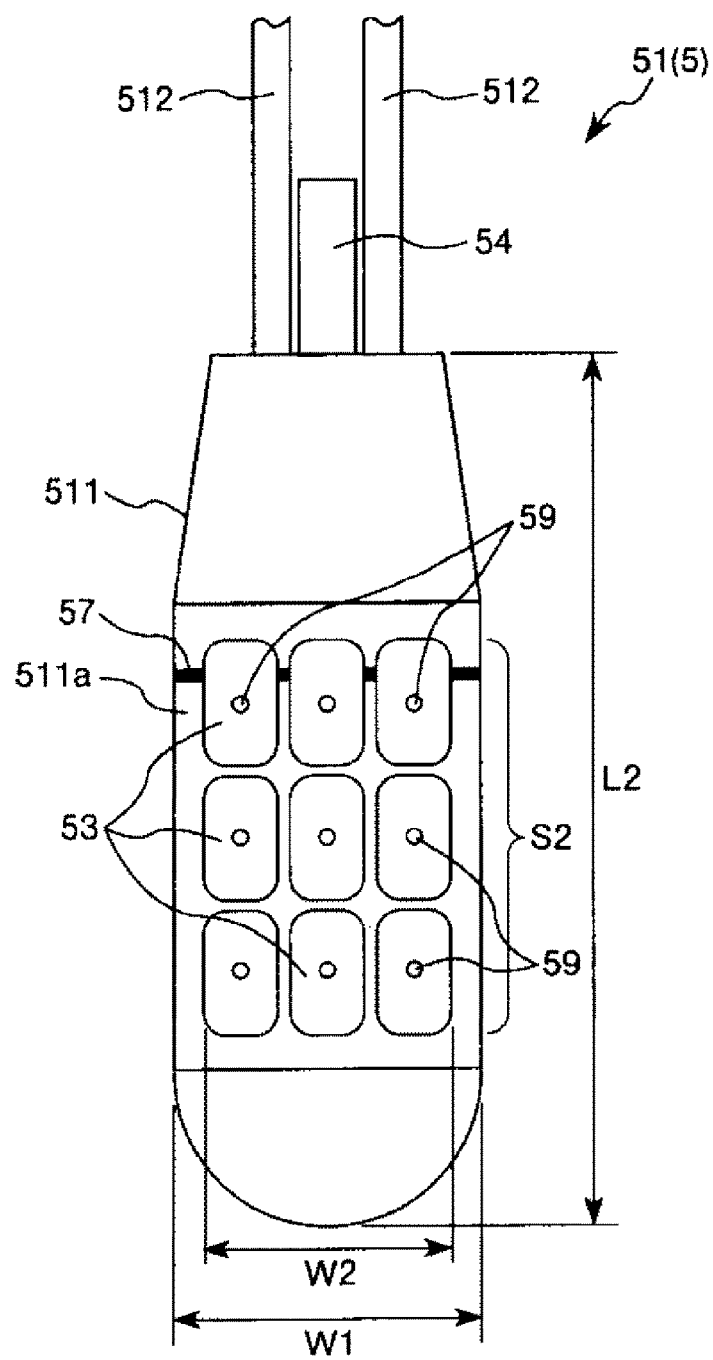
FIG. 16 is a partial enlarged view of a vaginal-insertion member possessed by the insertion tool shown in FIG. 14.

As shown in FIG. 16, the insertion section 511 has a flat shape crushed in the vertical direction of the puncture device 1 (in the direction in which the urethra and the vagina are arrayed). In accordance with an exemplary embodiment, the insertion section 511 can include a central portion which is substantially constant in width, and a distal portion which is somewhat rounded. The length L2 of the insertion section 511 is not particularly limited, and is preferably about 20 to 100 mm, more preferably about 30 to 60 mm. In accordance with an exemplary embodiment, the width W1 of the insertion section 511 is not specifically restricted, and is preferably about 10 to 40 mm, more preferably about 20 to 30 mm. Further, the thickness of the insertion section 511 is not particularly limited, and is preferably about 5 to 25 mm, more preferably about 10 to 20 mm. With the length, width and thickness set in these ranges, the insertion section 511 is made to have a shape and a size suited to general vaginas. Accordingly, the stability of the puncture device 1 in the mounted state is increased, and the burden on the patient can be reduced.

An upper surface (a surface on the urethral-insertion section 41 side) 511a of the insertion section 511 is formed with a plurality of bottomed recesses 53. Note that the number of the recesses 53 is not particularly limited, and, for example, only one recess may be provided. At a bottom surface of each recess 53, there is provided a single suction hole 59. Each suction hole 59 is connected to a suction port 54 provided at a proximal portion of the insertion section 511, by way of the inside of the insertion section 511. The suction port 54 is so provided as to be located outside the living body in the mounted state. A suction device such as a pump can be connected to the suction port 54. When the suction device is operated in a state where the insertion section 511 is inserted in the vagina, a vaginal anterior wall which is an upper surface of the vaginal wall is secured by suction onto the insertion section 511. When the vaginal-insertion section 51 is pushed in toward the distal side (into the body) with the vaginal wall thus fixed by suction, the vaginal wall can be pushed in as a result. Therefore, the disposition and shape of the vaginal wall can be conditioned, a puncture path for the puncture member 3 can be secured, and puncture by the puncture member 3 can be carried out relatively accurately and safely.

The region S2 where the plurality of recesses 53 are formed is disposed opposite to a region S1. The needle tip of the puncture member 3 passes between these regions S1 and S2. Since a urethral posterior wall (which is a lower surface of the urethral wall) is suction held onto the insertion section 411 in the region S1 as described before and the vaginal anterior wall is suction held onto the insertion section 511 in the region S2, the urethral wall and the vaginal wall are spaced wider apart from each other between the regions S1 and S2. Therefore, by passing the puncture member 3 through such a region, the puncture by the puncture member 3 can be performed relatively safely.

Figure 17A:
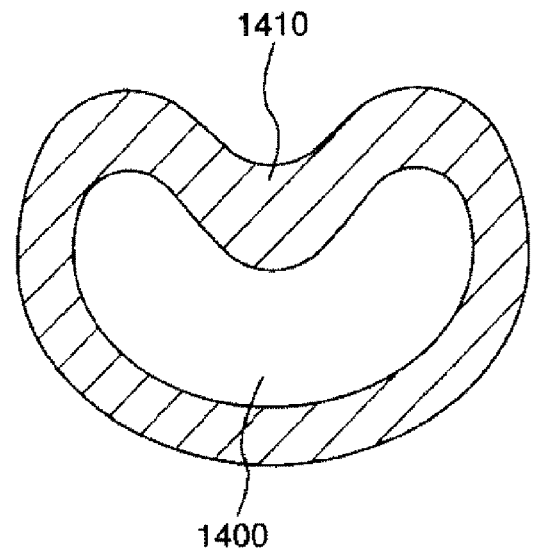
FIG. 17(a) is a sectional view showing an example of the shape of a vaginal wall.
Figure 17B:
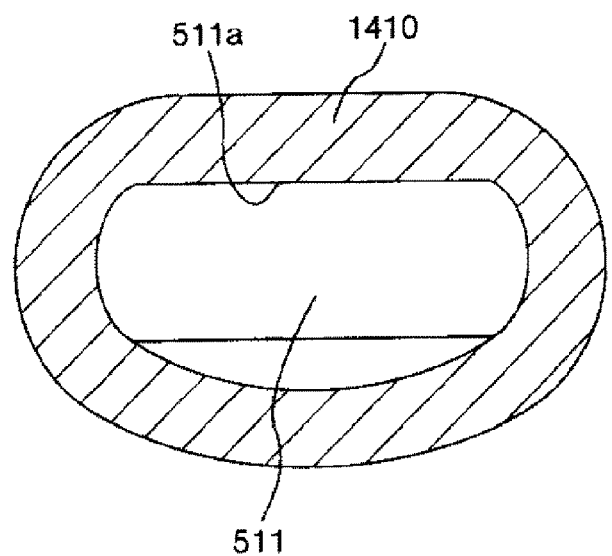
FIG. 17(b) is a sectional view showing a state where a vaginal-insertion section is inserted in a vagina shown in FIG. 17(a).

The region S2 stretches over substantially the whole range in the width direction of the upper surface 511a. The width W2 of the region S2 is not particularly limited, and is preferably about 9 to 39 mm, more preferably about 19 to 29 mm, which can help enable the vaginal anterior wall to be suction held onto the insertion section 511 more reliably, without being considerably influenced by the shape of the vaginal wall. For example, a patient may have a vagina 1400 shaped as shown in FIG. 17(a), wherein part of a vaginal anterior wall 1410 droops down into the inside of the vagina. Even in such a case, setting the width W2 as above-mentioned helps ensure that as shown in FIG. 17(b), not only the drooping-down part but also the parts on both sides of the drooping-down part can be suction held reliably. Therefore, the vaginal anterior wall can be spaced apart from the urethra more reliably, without being influenced by the shape of the vagina. Particularly, for example, in this embodiment, the insertion section 511 is flat shaped, so that the vaginal anterior wall can be suction held in the manner of being spaced farther away from the urethra, and the biological tissue between the urethral wall and the vaginal wall can be widened more widely.

In addition, the insertion section 511 is provided with a marker (puncture position confirmation section) 57 with which the puncture route of the puncture device 1 can be confirmed. In accordance with an exemplary embodiment, the puncture device can be fixed so as to puncture the region between the vaginal wall, which is present on the upper surface of the position where the marker 57 exists, and the urethral wall. As a result, the operability and safety of the insertion tool 6 are enhanced. The marker 57 is provided at least on a lower surface 511b of the insertion section 511. The lower surface 511b is a surface which is oriented toward the vaginal orifice side and is visible by the operator through the vaginal orifice, in the inserted state. With the marker 57 provided on the lower surface 511b, therefore, the puncture route of the puncture device 1 can be confirmed more reliably. In accordance with an exemplary embodiment, the depth of insertion of the insertion section 511 into the vagina can also be confirmed. Note that it is sufficient for the marker 57 to be visible externally, and the marker 57 can be configured as a colored part, a rugged part or the like.

The non-insertion section 512 is in the shape of a thin bar extending substantially in parallel to the urethral-insertion section 41. The spacing D between the non-insertion section 512 and the urethral-insertion section 41 is not particularly limited, and is preferably about 10 to 40 mm, correspondingly to the spacing between the urethral orifice and the vaginal orifice in general women.

The length of the non-insertion section 512 (the spacing between the vaginal orifice and the support section 50) is not specifically restricted, and is preferably not more than about 100 mm, more preferably in the range of about 20 to 50 mm. By this, the non-insertion section 512 can be made to have a suitable length, and its operability is enhanced. If the length of the non-insertion section 512 exceeds the above-mentioned upper limit, there may arise, depending on the configuration of the frame 2 or the like, a situation in which the center of gravity of the puncture device 1 is largely spaced from the patient and, accordingly, the stability of the puncture device 1 in the mounted state is lowered.

The support section 50 is provided with a male screw 501. With the male screw 501 fastened into a female screw (not illustrated) provided in the support section 40, the support sections 40 and 50 are fixed to each other.

The material constituting the vaginal-insertion member 5 is not specifically restricted. In this case, there can be used, for example, various metallic materials such as stainless steel, aluminum or aluminum alloys, titanium or titanium alloys, and various resin materials, like in the case of the urethral-insertion member 4.

The configuration of the puncture device 1 has thus been described above.

Note that while the urethral-insertion member 4 and the vaginal-insertion member 5 constituting the insertion tool 6 have been configured to be attachable to and detachable from each other in the puncture device 1, this configuration is not restrictive. The urethral-insertion member 4 and the vaginal-insertion member 5 may be so configured that they cannot be attached to or detached from each other.

In addition, while the urethral-insertion section 41 is fixed relative to the support section 40 in the puncture device 1, this configuration is not restrictive. A configuration may be adopted wherein a state where the urethral-insertion section 41 is fixed relative to the support section 40 and a state where the urethral-insertion section 41 is slidable in the axial direction relative to the support section 40 can be selected. In accordance with an exemplary embodiment, for example, a configuration may be adopted wherein loosening a screw provided on the support section 40 results in a state where the urethral-insertion section 41 is slidable relative to the support section 40 and wherein fastening the screw results in a state where the urethral-insertion section 41 is fixed relative to the support section 40. According to this configuration, the length of the non-insertion section 412 can be adjusted, so that a user-friendly insertion tool 6 is realized. Note that the same applies to the vaginal-insertion section 51.

In accordance with an exemplary embodiment, while the component members are fixed to the frame 2 so that the inclination angle θ2 is constant in the puncture device 1, this configuration is not restrictive, and the inclination angle θ2 may be variable. Where the inclination angle θ2 is variable, the inclination angle θ2 can be adjusted according to the patient, so that a user-friendly puncture device 1 is realized.

A method of using the puncture device 1 will be described below. Prior to the description of the using method, the implant 9 to be used with the puncture device 1 will be described.

Figure 18:
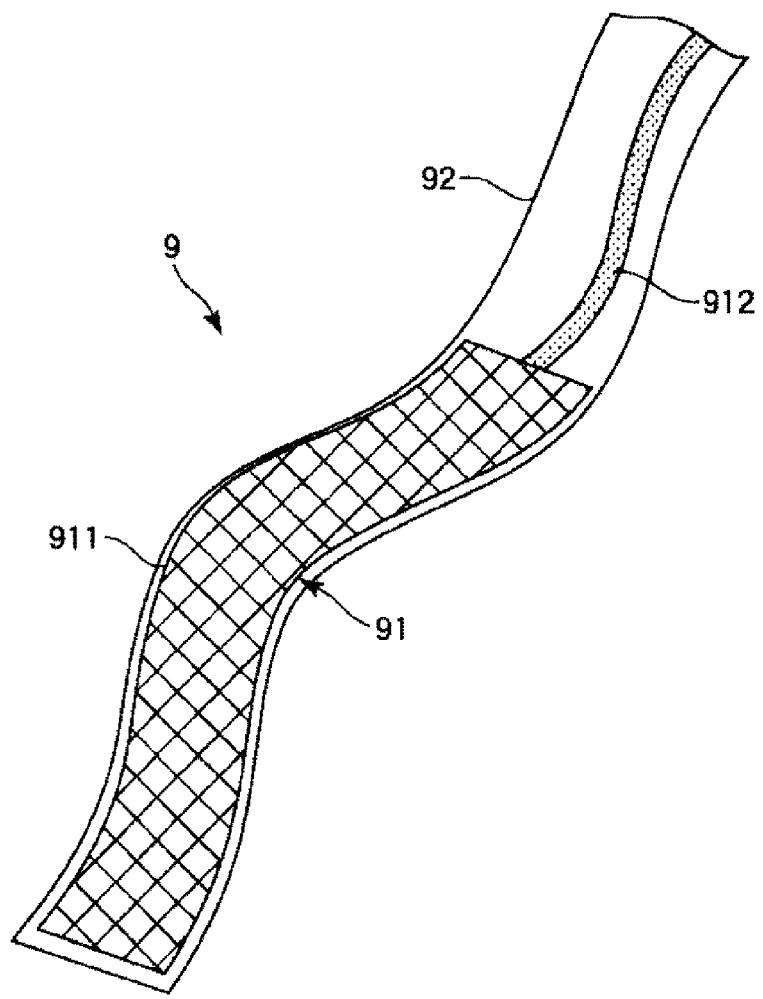
FIG. 18 illustrates an implant to be used with the puncture device shown in FIG. 1.

An implant (biological tissue-supporting indwelling article) 9 shown in FIG. 18 is an embeddable instrument for treatment of female urinary incontinence, for example, an instrument for supporting the urethra. For example, the implant 9 is an instrument which, when the urethra is going to move toward the vaginal wall side, supports the urethra so as to restrict its movement in the direction for coming away from the vaginal wall. As the implant 9, for example, a flexible elongated body can be used.

The implant 9 can include the implant main body (belt-shaped elongated article) 91, and a bag-shaped wrapping material 92 for accommodating the implant main body 91. In addition, the implant main body 91 can include the main body section 911, and a ribbon 912 interlocked to one end of the main body section 911. With the implant 9 provided with the wrapping material 92, contamination of the implant main body 91 can be prevented effectively. Note that a guide wire, a cord, or a string may be used in place of the ribbon 912.

The main body section 911 is net-like in form, and is belt-like in overall shape. Note that the main body section 911 may be composed, for example, of a network-like knitted body knitted by causing linear elements to intersect, for example, network-formed braiding. Examples of the linear element include those which are circular in cross section, and those which are flat shaped in cross section, for example, belt-shaped (ribbon-shaped) ones.

The materials constituting the main body section 911, the ribbon 912 and the wrapping material 92 are not particularly limited. For example, various resin materials which are biocompatible such as polypropylene, polyesters, nylon, and fibers can be used as the materials.

Note that the implant 9 is not limited to the above-mentioned network-formed one, so long as the same or equivalent effect can be exhibited. The implant 9 and the sheath 30 as above constitute an intrapelvic treatment kit of the present disclosure.

An operating procedure of the puncture device 1, for example, a procedure for embedding the implant 9 into a living body will be described.

Figure 19A:
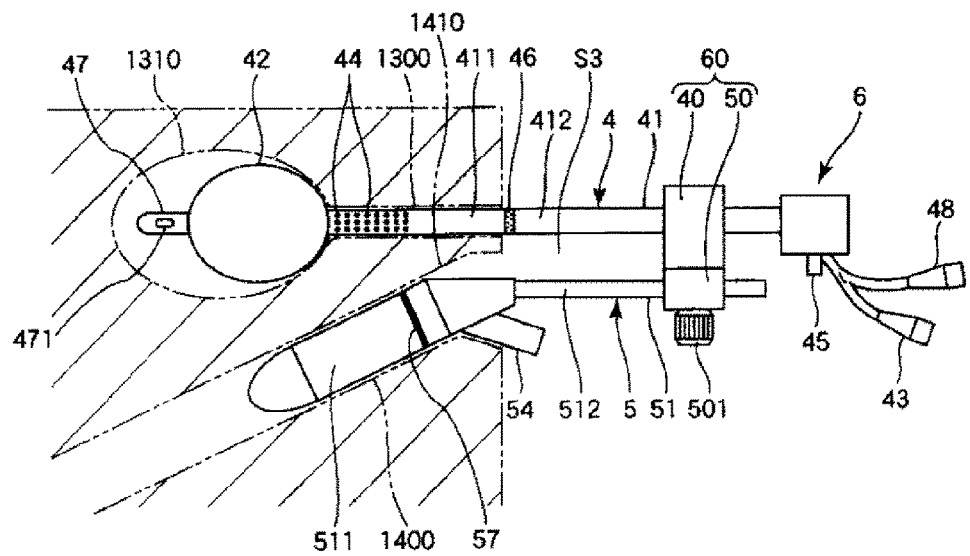
FIGS. 19(a) and 19(b) are each views for explaining an operating procedure of the puncture device shown in FIG. 1.

First, a patient is placed in a lithotomy position on an operating table, and the insertion tool 6 is mounted onto the patient, as depicted in FIG. 19(a). In accordance with an exemplary embodiment, first, the urethral-insertion section 41 of the urethral-insertion member 4 is inserted into the patient's urethra 1300. In this case, the depth of insertion is confirmed with the marker 46, and the balloon 42 is disposed inside the bladder 1310. The urethra 1300 is corrected into a predetermined shape by the urethral-insertion section 41 having the predetermined shape. In the case of this embodiment, the urethra is corrected into a rectilinear shape by the urethral-insertion section 41 which is rectilinear in shape.

Next, the balloon 42 is expanded, and urine is drained from within the bladder 1310 via the drain hole 471, as required. In accordance with an exemplary embodiment, the vaginal-insertion section 51 of the vaginal-insertion member 5 is inserted into the patient's vagina 1400. In this case, the puncture position is confirmed with the marker 57, and insertion into a suitable depth is performed. Then, the support sections 40 and 50 are fixed by operating the male screw 501. By this, the mounting of the insertion tool 6 onto the patient is completed. In this state, the non-insertion sections 412 and 512 are spaced apart from each other, and, further, the support section 60 is spaced apart from a body surface between the urethral orifice and the vaginal orifice, so that the body surface is exposed. In addition, in the case where the insertion section 511 and the vaginal anterior wall are spaced apart from each other to form a gap (space) therebetween, there is formed a space S3 for permitting a syringe to puncture the biological tissue between the urethra and the vagina via the body surface between the urethral orifice and the vaginal orifice.

Subsequently, suction devices are connected to the suction ports 45 and 54, and the suction devices are operated, to suction hold the urethral posterior wall onto the urethral-insertion section 41 and suction hold the vaginal anterior wall onto the vaginal-insertion section 51. For example, when the urethral posterior wall is suction held onto the urethral-insertion section 41 properly, the suction holes 44 are closed with the urethral wall, so that the suction via the suction port 45 is stopped or weakened. Similarly, when the vaginal anterior wall is suction held onto the vaginal-insertion section 51 properly, the suction holes 59 are closed with the vaginal wall, so that the suction via the suction port 54 is stopped or weakened. Therefore, on the basis of the manners of suction via the suction ports 45 and 54 (for example, on the basis of the magnitudes of the sounds generated upon the suction), the operator can check whether or not the urethral posterior wall and the vaginal anterior wall are suction held onto the urethral-insertion section 41 and the vaginal-insertion section 51 properly. Note that the insertion tool 6 may be provided with a checking mechanism for mechanically checking the suction-held state. The checking mechanism is not specifically restricted, so long as the suction-held state can be checked by use of the mechanism. For example, there may be adopted a configuration including a flow rate measuring section (negative pressure meter) for measuring the flow rate through the suction port 54, and a determining section for determining whether or not the suction holding is performed properly, on the basis of the measurement results supplied from the flow rate measuring section.

Figure 19B:
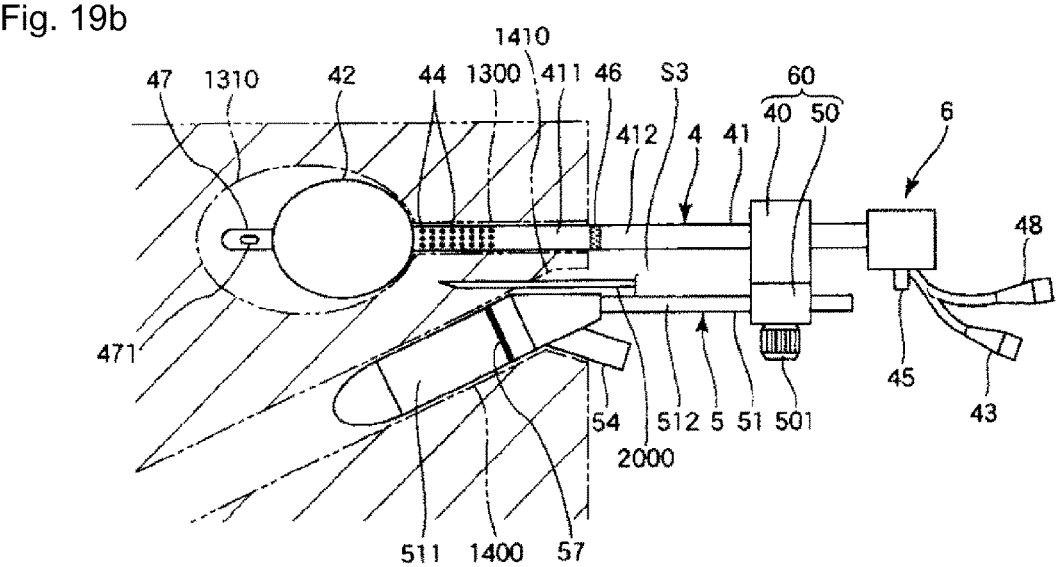

Next, liquid dissection is conducted. In accordance with an exemplary embodiment, as shown in FIG. 19(b), a puncture needle of a syringe 2000 is made to puncture the vaginal anterior wall 1410 through the space (space S3) between the insertion section 511 and the vaginal anterior wall 1410, and a liquid such as physiological saline or local anesthetic is injected into the biological tissue in a region between the urethra 1300 and the vagina 1400 (a region between the region S1 and the region S2). As a result, the biological tissue between the regions S1 and S2 is expanded, the urethral posterior wall is pressed against the urethral-insertion section 41, and the vaginal anterior wall 1410 is pressed against the vaginal-insertion section 51.

Here, it is preferable to continue the suction via the suction holes 44 and 59 even during the liquid dissection. When the urethral posterior wall is pressed against the urethral-insertion section 41 by the liquid dissection, the urethral posterior wall is suction held onto the urethral-insertion section 41 more securely, so that the suction through the suction port 45 is stopped or weakened. Similarly, when the vaginal anterior wall is pressed against the vaginal-insertion section 51, the vaginal anterior wall is suction held onto the vaginal-insertion section 51 more securely, so that the suction through the suction port 45 is stopped or weakened. Therefore, on the basis of the manners of suction via the suction ports 45 and 54, the operator can check whether or not the liquid dissection is performed properly.

Figure 20A:
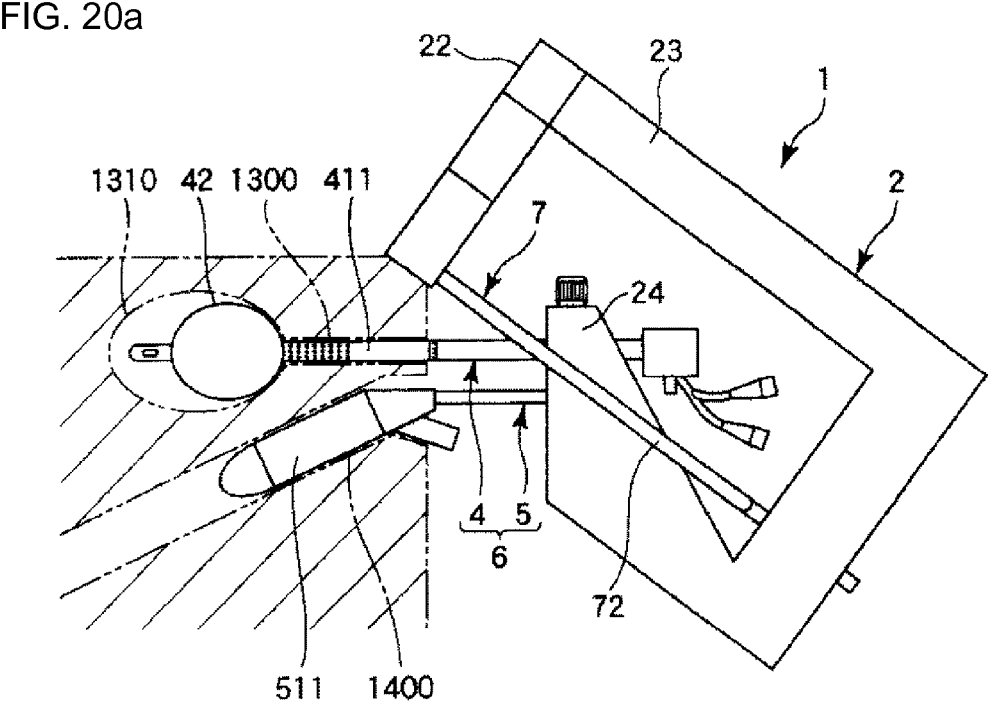
FIGS. 20(a) and 20(b) are views for explaining the operating procedure of the puncture device shown in FIG. 1.
Figure 20B:
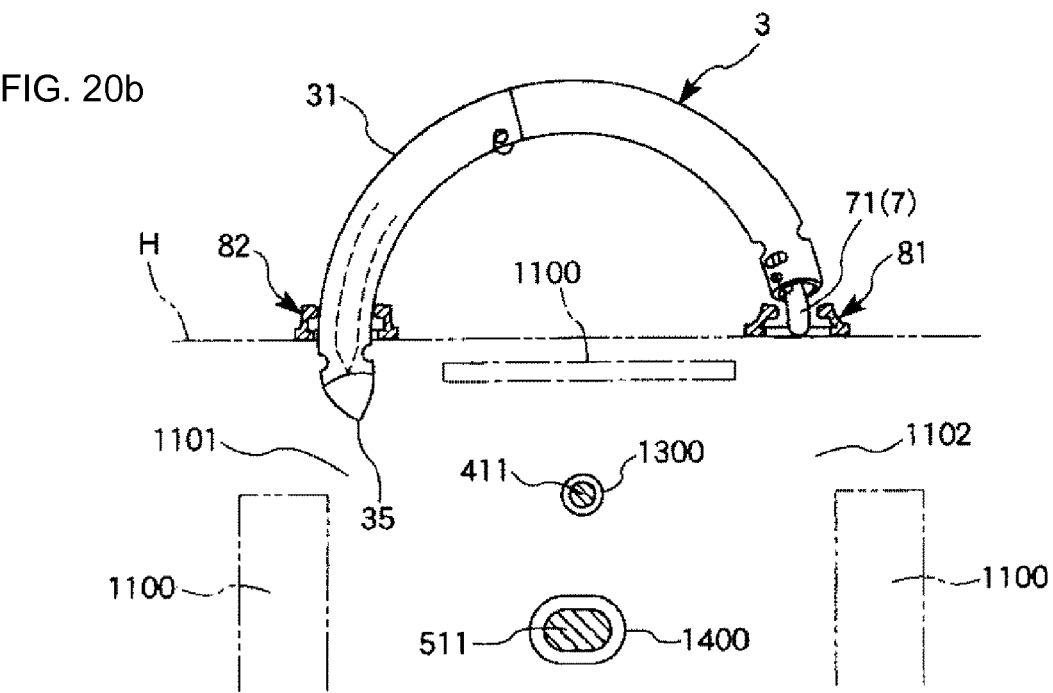
Figure 21:
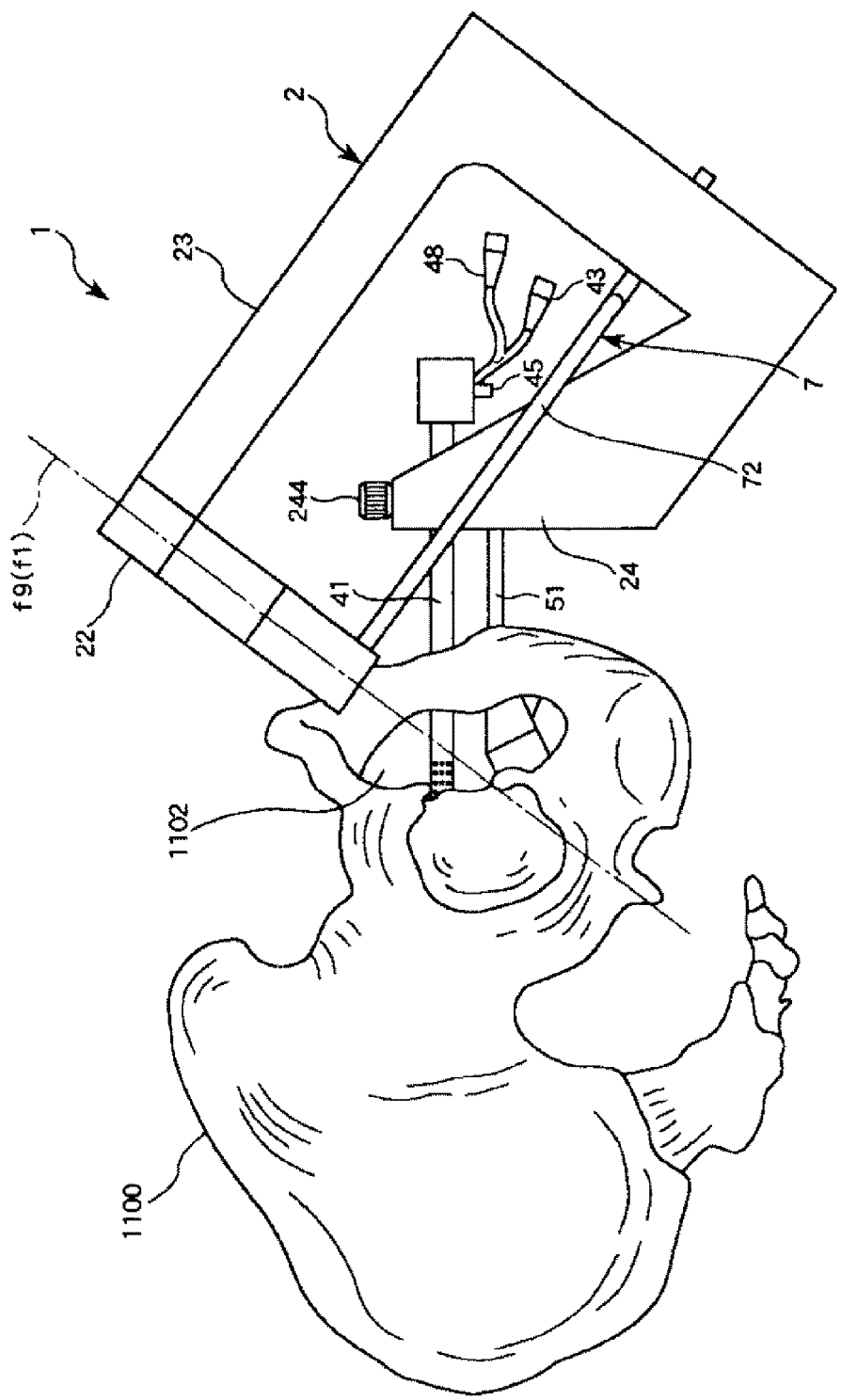
FIG. 21 is a side view showing the relation between the puncture device and the pelvis at the time of the state shown in FIG. 20(a).

After the liquid dissection is performed and the urethral posterior wall and the vaginal anterior wall are sufficiently spaced apart, the frame 2 is fixed to the insertion tool 6, as shown in FIG. 20. This results in a state in which the puncture device 1 is mounted onto the patient. In this state, the positional relation between the pelvis 1100 and the puncture device 1 is as depicted in FIG. 21.

Figure 22A:
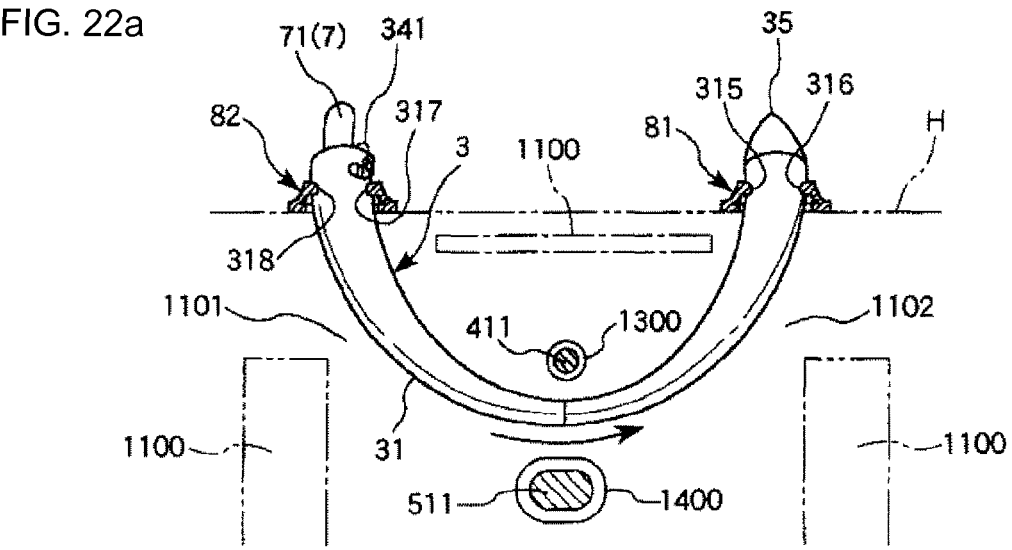
FIGS. 22(a) and 22(b) are each views for explaining the operating procedure of the puncture device shown in FIG. 1.
Figure 23:
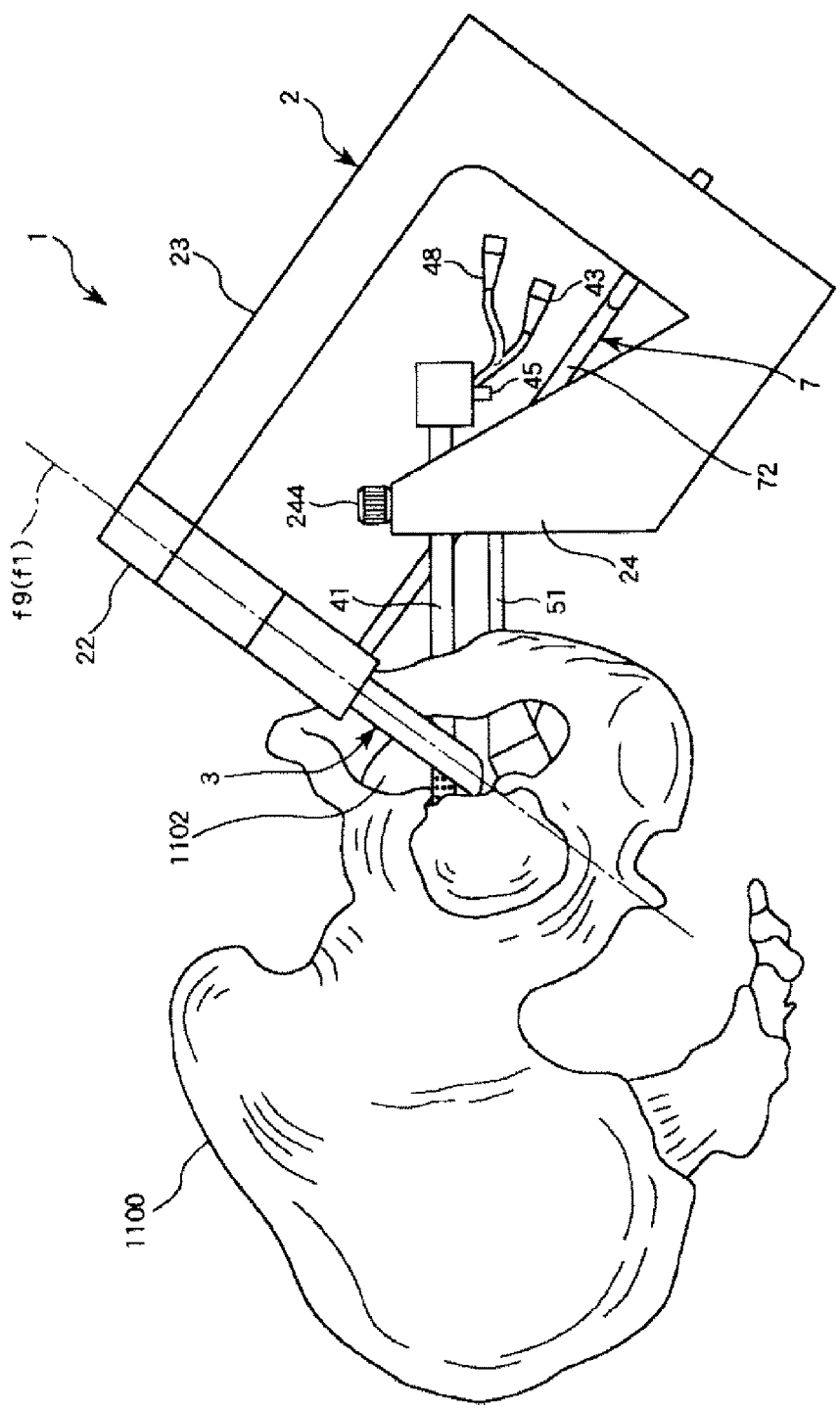
FIG. 23 is a side view showing the relation between the puncture device and the pelvis at the time of the state shown in FIG. 22(a).

Subsequently, for example, while gripping the interlock section 23 of the frame 2 by one hand, the interlock section 72 of the operating member 7 is grasped by the other hand, and, as shown in FIG. 22(a), the operating member 7 is rotated counterclockwise, which causes the needle body 35 of the puncture member 3 to puncture a body surface H at a part (first part) in an inguinal region on the right side of the patient or near the inguinal region, thereby entering the body, to sequentially pass an obturator foramen 1101 on one side, between the urethra 1300 and the vagina 1400, and an obturator foramen 1102 on the other side, then to exit the body via the body surface H at a part (second part) in an inguinal region on the left side or near this inguinal region, and finally to evacuate into the guide section 22 (see FIG. 23).

As a result, the puncture member 3 is disposed in the living body, and, by the aforementioned principle, the anchors 81 and 82 are engaged with the main body 31. Therefore, the anchor 82 abuts on the body surface H, whereby further insertion of a proximal portion of the main body 31 into the living body is restrained. In accordance with an exemplary embodiment, the state where the proximal end of the main body 31 is exposed outside of the living body can be secured.

Figure 22B:
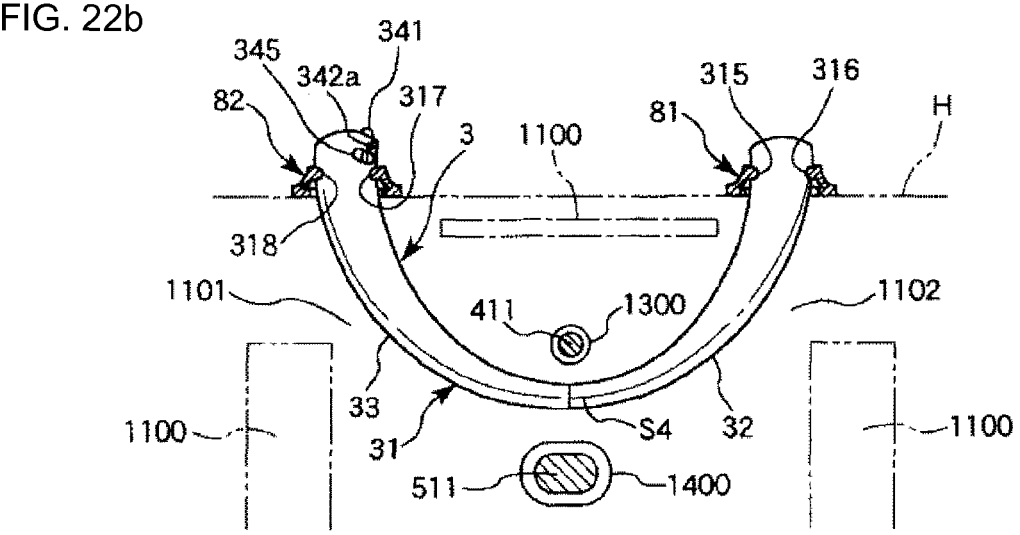

Next, the operating member 7 is rotated clockwise in FIG. 22(a). In this case, although the puncture member 3 also tends to rotate clockwise together with the operating member 7, the abutment of the anchor 81 against the body surface H prevents further rotation (movement) of the puncture member 3. Therefore, while the state where the distal end of the main body 31 is exposed outside of the living body is maintained, the insertion section 71 is drawn out of the puncture member 3 and the living body. Subsequently, the puncture device 1 (other members than the puncture member 3) is dismounted from the patient, and, further, the needle body 35 is detached from the main body 31, which results in a state in which only the main body 31 is disposed inside the living body, as shown in FIG. 22(b). The main body 31 is disposed inside the living body, with both the distal-side opening and the proximal-side opening exposed outside of the living body.

Figure 24:
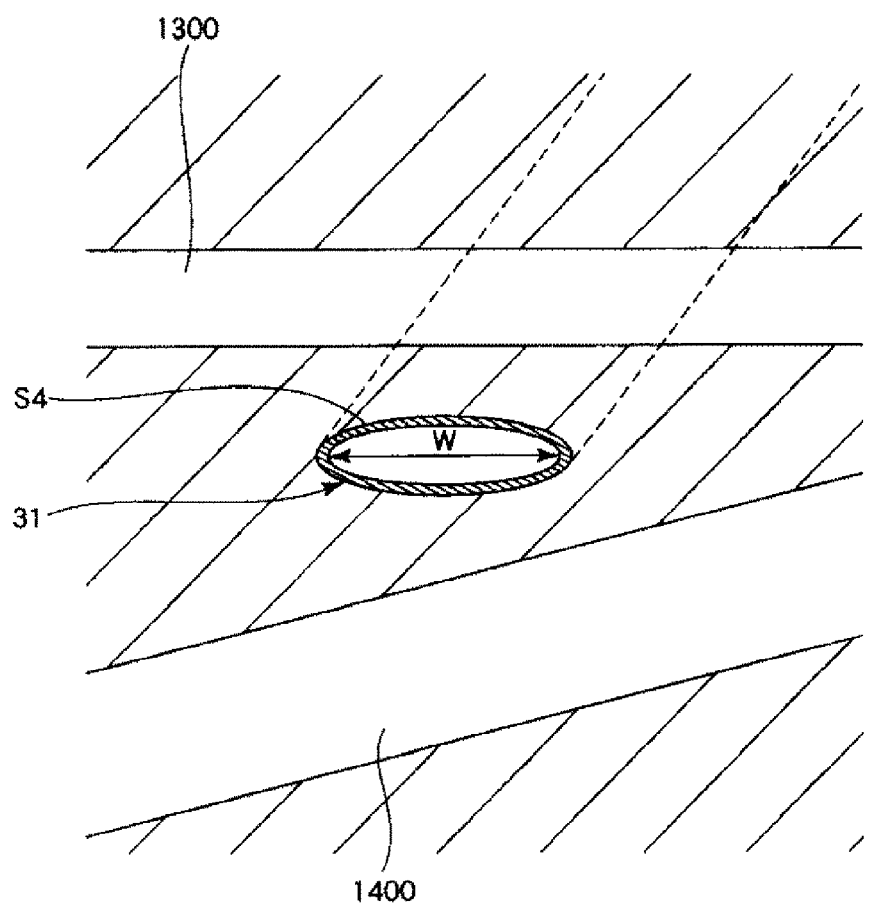
FIG. 24 is a sectional view showing the posture of the puncture member relative to a urethra at the time of the state shown in FIG. 22(b).

Subsequently, the position of the main body 31 is adjusted, as required. In accordance with an exemplary embodiment, the main body 31 is shifted toward the proximal side or the distal side so that the positions of the anchors 81 and 82 relative to the living body will be in left-right symmetry. By this, the central portion S4 of the main body 31 can be positioned between the urethra 1300 and the vagina 1400 more reliably. In this state, as shown in FIG. 24, the central portion S4 is so disposed that its width direction (the direction of the major axis J32) W is substantially parallel to the urethra 1300. In accordance with an exemplary embodiment, the urethra 1300 corrected in shape by the insertion of the urethral-insertion member 4 therein and the width direction W of the central portion S4 are substantially parallel to each other.

Figure 25A:
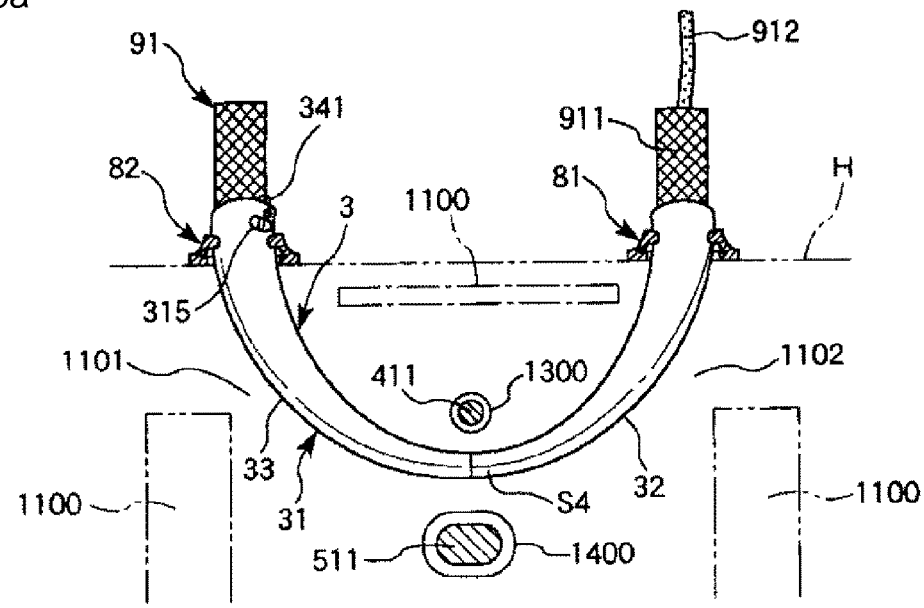
FIGS. 25(a) and 25(b) are each views for explaining the operating procedure of the puncture device shown in FIG. 1.
Figure 25B:
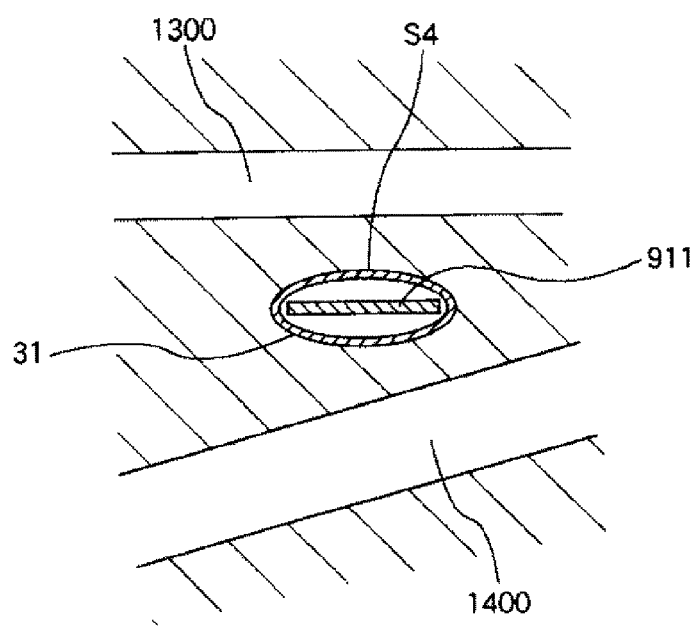

Next, while taking the implant main body 91 out of the wrapping material 92, the implant main body 91 is inserted into the main body 31, and a state where the ribbon 912 is protruded from the proximal-side opening and the distal-side opening of the main body 31 is established, as shown in FIG. 25(a). Thus, the implant main body 91 is kept accommodated inside the wrapping material 92 until immediately before disposed inside the main body 31, whereby contamination of the implant main body 91 can be prevented. Note that, as described above, since the main body 31 is flat shaped, the posture of the main body section 911 follows this flat shape. In accordance with an exemplary embodiment, as shown in FIG. 25(*b*), the main body section 911 is disposed inside the main body 31 in such a manner that its width direction coincides with the width direction of the main body 31. As for the relation with the urethra 1300, the implant main body 91 is disposed in parallel to the urethra 1300 which has been corrected in shape.

Figure 26A:
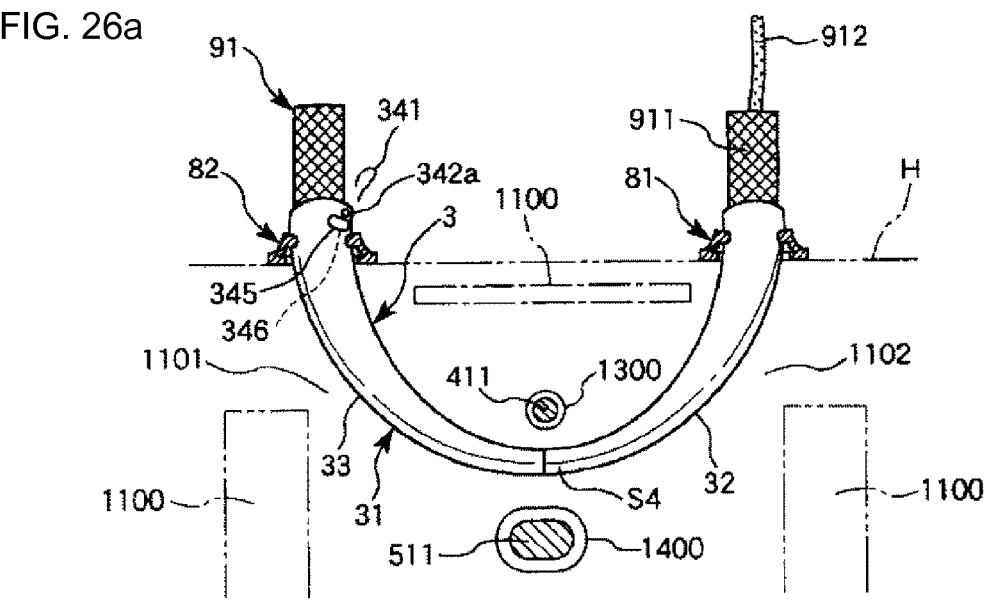
FIGS. 26(a) and 26(b) are each views for explaining the operating procedure of the puncture device shown in FIG. 1.
Figure 26B:
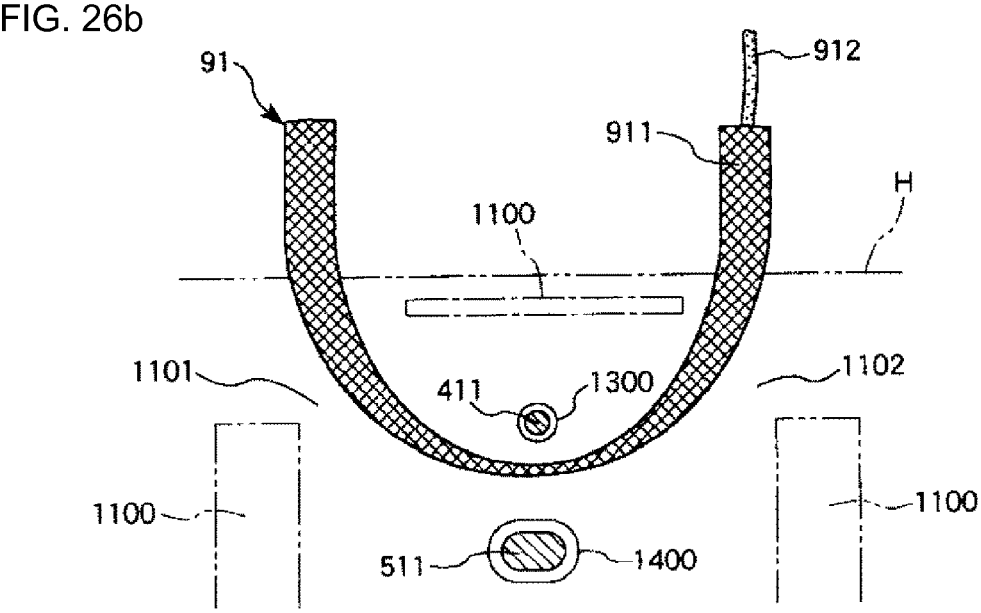

Subsequently, as shown in FIG. 26(*a*), the string 341 exposed from the exposure holes 345 and 346 is cut. This results in a state in which the main body 31 can be separated into the distal separable piece 32 and the proximal separable piece 33. Note that the exposure holes 345 and 346 are located on the proximal side as compared with the anchor 82 and, therefore, can be exposed outside of the living body. Accordingly, the cutting of the string 341 can be carried out relatively easily.

Next, the suction holding of the urethral posterior wall by the urethral-insertion section 41 and the suction holding of the vaginal anterior wall 1410 by the vaginal-insertion section 51 are stopped. As a result, the positions and shapes of the urethra 1300 and the vagina 1400 are returned into the original natural states.

Subsequently, the connection between the distal separable piece 32 and the proximal separable piece 33 is released, the distal separable piece 32 is drawn out of the living body toward the distal side, and the proximal separable piece 33 is drawn out of the living body toward the proximal side. In this case, the distal separable piece 32 and the proximal separable piece 33 are substantially simultaneously moved in opposite directions, and the distal separable piece 32 and the proximal separable piece 33 are moved in circular arc courses along their shapes, respectively. By this, the main body 31 is smoothly removed out of the living body. As the distal separable piece 32 and the proximal separable piece 33 are gradually removed out of the living body as aforementioned, the surrounding tissue having been pushed open by the main body 31 returns into its original position, and the tissue comes into contact with the implant main body 91 gradually from a central portion toward both end portions of the implant main body 91. As aforementioned, the distal separable piece 32 and the proximal separable piece 33 are moved in the directions along their shapes, and the main body 31 is provided with the internal space in which the implant main body 91 can be moved with sufficiently low friction. This enables the implant main body 91 to be left indwelling as it is, without any unnecessary tension exerted thereon. As a result, it is unnecessary to adjust a tension on the implant main body 91. The above operations result in a state in which the implant main body 91 is embedded in the living body, as shown in FIG. 26(*b*).

In the state where the implant main body 91 is embedded inside the living body, the main body section 911 is disposed substantially in parallel to the urethra 1300, in a region between the urethra 1300 and the vagina 1400. Therefore, the urethra 1300 can be supported in a wider area by the implant main body 91.

Thus, by removing the main body 31 out of the living body through dividing the main body 31, the main body 31 can be relatively easily drawn out of the living body. In addition, since the main body 31 can be drawn out of the living body without need to remove the anchors 81 and 82 from the main body 31, the main body 31 can be drawn out easily. In accordance with an exemplary embodiment, according to such a drawing-out method, the separable pieces 32 and 33 being drawn out exert little influence on the posture of the main body section 911 in the region between the urethra 1300 and the vagina 1400.

In addition, since the separable pieces 32 and 33 are drawn out of the living body in the state where the urethral-insertion member 4 is inserted in the urethra 1300, excessive tension can be prevented from being exerted on the urethra 1300 by the implant main body 91 placed indwelling in the living body.

Next, the urethral-insertion member 4 is drawn out of the urethra 1300, and the vaginal-insertion member 5 is drawn out of the vagina 1400. After the urethral-insertion member 4 is drawn out, the urethra 1300 returns into its shape in the natural state. Since the main body section 911 is embedded in the tissue, however, a state in which the urethra 1300 in the natural state and the main body section 911 are parallel can be maintained.

Thereafter, unnecessary portions of the implant main body 91 can be cut away, to finish the procedure.

As has been described above, according to the puncture device 1, placement of the implant 9 indwelling can be dealt with by only low-invasive procedures such as puncture by the puncture member 3, and without need for high-invasive procedures such as incision. Therefore, the burden on the patient is light, and the safety of the patient is high. In addition, since the implant main body 91 can be embedded in parallel to the urethra 1300, the urethra 1300 can be supported in a wider area. In accordance with an exemplary embodiment, the living body can be punctured by the puncture member 3 while avoiding the urethra 1300 and the vagina 1400, so that puncture of the urethra 1300 or the vagina 1400 with the puncture member 3 can be prevented from occurring, and safety is therefore relatively ensured. Further, unlike in the case of conventional incision of the vagina, a situation can be avoided in which the implant 9 would be exposed to the inside of the vagina via a wound caused by the incision, or a situation in which complications would be generated such as infection from the wound. Thus, relatively high safety can be ensured, and the implant 9 can be reliably embedded.

Figure 27:
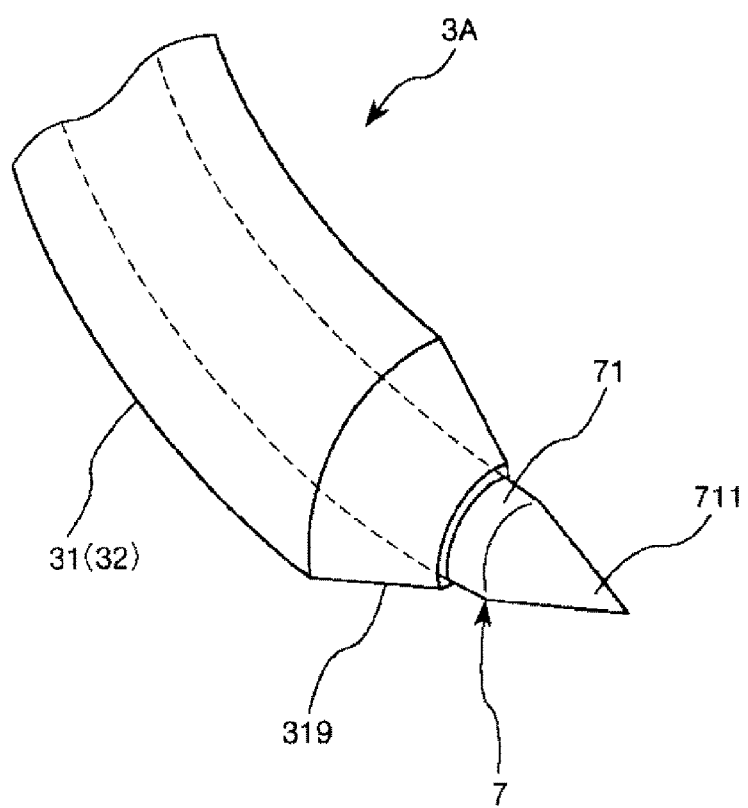
FIG. 27 is a perspective view showing a medical tube (medical tube assembly) according to a second embodiment of the present disclosure.
Figure 28:
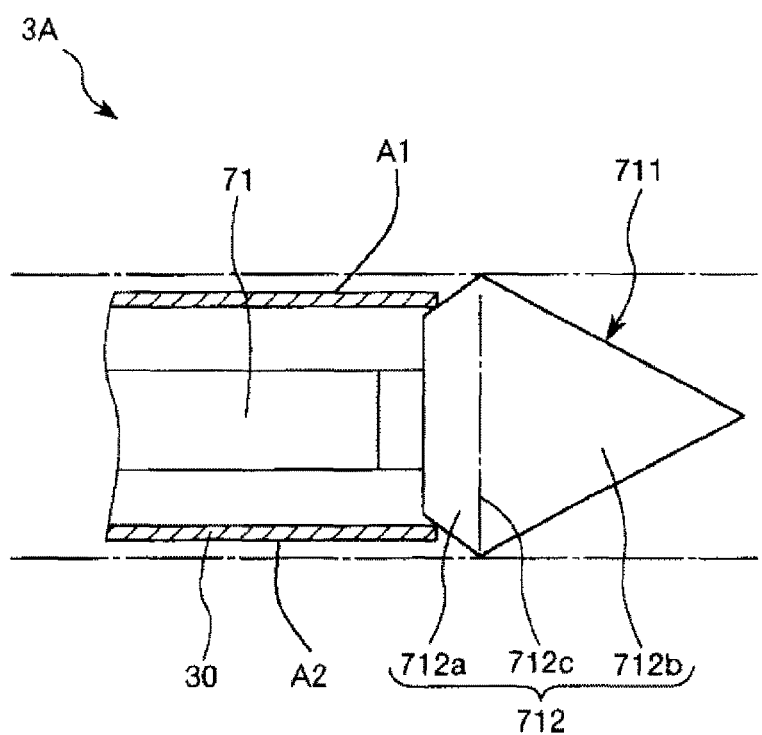
FIG. 28 is a sectional view showing a modification of the medical tube (medical tube assembly) shown in FIG. 27.

Referring to FIGS. 27 and 28, the second embodiment of a puncture device will be described below. The following description will center on differences from the aforementioned embodiment, and descriptions of the same items as above will be omitted.

This embodiment is the same as the aforementioned first embodiment, except mainly for differences in the configuration of puncture member.

As shown in FIG. 27, a puncture member 3A in this embodiment is composed of a sheath 30. In accordance with an exemplary embodiment, the puncture member 3A is configured by omitting the needle body 35 from the puncture member 3A in the aforementioned first embodiment. In addition, in a state (initial state) where an insertion section 71 is inserted in the puncture member 3A, a distal portion 711 as a distal portion of the insertion section 71 is protruding from a distal-side opening of a main body 31. The distal portion 711 protruding from the main body 31 can function as a needle tip of the puncture member 3A. With the distal portion 711 of the insertion section 71 thus functioning also as the needle body of the puncture member 3A, the number of members can be reduced as compared with the aforementioned first embodiment, for example. In accordance with an exemplary, when the puncture member 3 is made to puncture a living body and the insertion section 71 is drawn out of the puncture member 3, the distal-side opening of the main body 31 can be opened. In accordance with an exemplary embodiment, unlike in the aforementioned first embodiment, in this embodiment, the needle body 35 does not need to be detached in order to open the distal-side opening of the main body 31, and, accordingly, the operation can be carried out smoothly. In addition, the outside diameter of the insertion section 71 and the inside diameter of the distal-side opening of the main body 31 can be set to be substantially the same, so that slippage of the insertion section 71 relative to the main body 31 can be prevented and, hence, operability is enhanced.

In accordance with an exemplary embodiment, the main body 31 is provided at its distal portion with a tapered section 319 where its outside diameter gradually increases along the proximal direction from its distal-side opening. The tapered section 319 functions as a dissecting section which, as the distal portion 711 of the insertion section 71 punctures a living body, dissects the living body in the manner of gradually expanding the living body, following the distal portion 711.

Note that while the taper angle of the tapered section 319 and the taper angle of the distal portion 711 may be the same, they are preferably different from each other as shown in FIG. 27. In this case, it is preferable that the taper angle of the tapered section 319 is smaller than the taper angle of the distal portion 711. This configuration enables smooth puncture.

According to the second embodiment as above, also, the same or equivalent effects to those of the aforementioned first embodiment can be produced.

In addition, as a modification of this embodiment, the following configuration may be mentioned. As shown in FIG. 28, a puncture member 3A is composed of a sheath 30. In accordance with an exemplary embodiment, the puncture member 3A is configured by omitting the needle body 35 from the puncture member 3A in the aforementioned first embodiment. In accordance with an exemplary embodiment, in a state (initial state) where an insertion section 71 is inserted in the puncture member 3, a distal portion 711 as a distal portion of the insertion section 71 is protruding from a distal-side opening of a main body 31.

The distal portion 711 is provided in a detachable manner in relation to the insertion section 71, through screw engagement, fitting or the like. In addition, the distal portion 711 has a needle tip 712 protruding from the distal end of the sheath 30. The needle tip 712 has a flat shape modeled after the sheath 30. In accordance with an exemplary embodiment, the needle tip 712 can include a gradually increasing area section 712a where its cross-sectional area gradually increases toward its distal end; and a gradually decreasing area section 712b which is provided on the distal side of the gradually increasing area section 712a and in which its cross-sectional area gradually decreases toward its distal end. The minor axis of a boundary 712c between the gradually increasing area section 712a and the gradually decreasing area section 712b is longer than the minor axis at the distal end of the sheath 30, and the major axis of the boundary 712c is longer than the major axis at the distal end of the sheath 30, which can help ensure that the inside of a living body can be punctured substantially by only the needle tip 712. Therefore, puncture resistance can be reduced, and a living body can be punctured smoothly. Note that the minor axis of the boundary 712c may be equal to the minor axis at the distal end of the sheath 30, and the major axis of the boundary 712c may be equal to the major axis at the distal end of the sheath 30.

Figure 29:
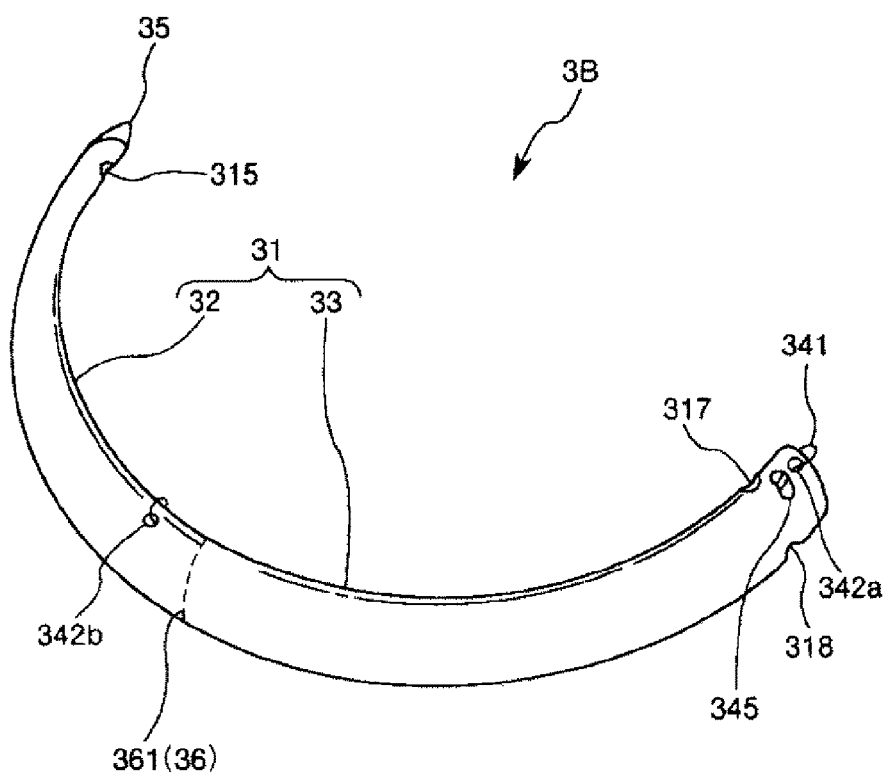
FIG. 29 is a perspective view showing a medical tube (medical tube assembly) according to a third embodiment of the present disclosure.

Referring to FIG. 29, the third embodiment of a puncture device will be described below. The following description will center on differences from the aforementioned embodiments, and descriptions of the same items as above will be omitted.

This embodiment is the same as the aforementioned first embodiment, except mainly for differences in the configuration of puncture member.

As shown in FIG. 29, a main body 31 of a puncture member 3B has a configuration wherein a distal separable piece 32 and a proximal separable piece 33 are connected with each other through a brittle section 36. In this embodiment, the distal separable piece 32, the proximal separable piece 33 and the brittle section 36 are formed integrally. The configuration of the brittle section 36 is not particularly limited, so long as the brittle section 36 is more brittle and easier to break than the distal separable piece 32 and the proximal separable piece 33. For example, the brittle section 36 may be configured to have perforations 361 provided along the entire circumference of the main body 31.

For instance, when the distal separable piece 32 grasped by one hand and the proximal separable piece 33 grasped by the other hand are pulled away from each other, the brittle section 36 is broken, and the distal separable piece 32 and the proximal separable piece 33 are separated from each other. According to such a configuration, the overlapping of the distal separable piece 32 and the proximal separable piece 33 with each other as in the aforementioned first embodiment can be avoided. Therefore, no step is generated at the boundary between the distal separable piece 32 and the proximal separable piece 33, so that puncture by the puncture member 3B and insertion and passage of an implant main body 91 into and through the main body 31 can be performed smoothly. In addition, since the brittle section 36 can function as a state maintaining mechanism for maintaining the connected state of the distal separable piece 32 and the proximal separable piece 33, the state maintaining mechanism 34 as in the aforementioned first embodiment can be omitted. Consequently, the configuration of the puncture member 3B can be simplified.

According to the third embodiment as above, also, the same or equivalent effects to those of the aforementioned first embodiment can be produced.

Figure 30:
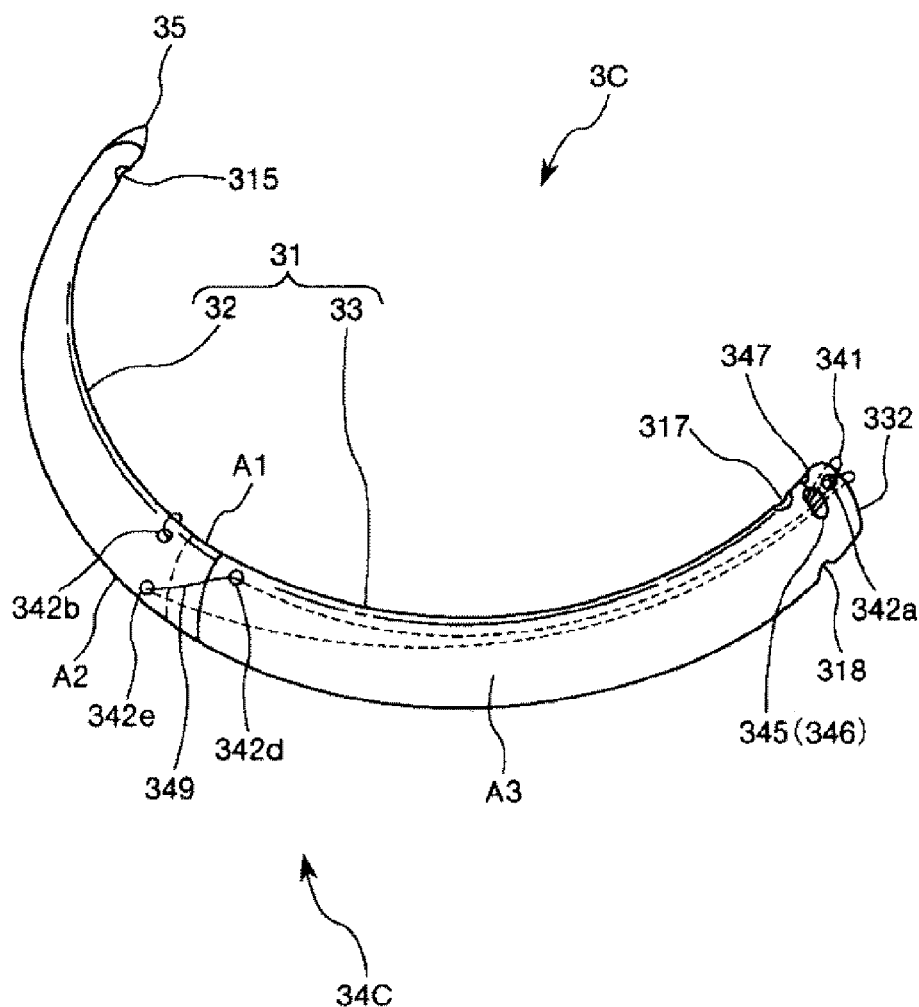
FIG. 30 is a perspective view showing a medical tube (medical tube assembly) according to a fourth embodiment of the present disclosure.

Referring to FIG. 30, the fourth embodiment of a puncture device will be described below. The following description will center on differences from the aforementioned embodiments, and descriptions of the same items as above will be omitted.

This embodiment is the same as the aforementioned first embodiment, except mainly for differences in the configuration of puncture member.

As shown in FIG. 30, a state maintaining mechanism 34C possessed by a puncture member 3C in this embodiment further can include holes 342d and 342e and an endless string (connecting member) 349 inserted in and passed through the holes 342d and 342e, in addition to the state maintaining mechanism 34 in the aforementioned first embodiment.

The hole 342d is provided in a distal portion of a proximal separable piece 33, at a position near an inner circumferential portion A1 of a front surface A3. In accordance with an exemplary embodiment, the hole 342e is provided in a proximal portion of a distal separable piece 32, at a position near an outer circumferential portion A2 of the front surface A3.

The string 349 is mostly disposed inside a main body 31, and is exposed outside of the main body 31 between the hole 342d and the hole 342e and between a hole 342a and a proximal-side opening 332. The string 349 can be obtained, for example, by preparing a string having ends, inserting one end of the string into the main body 31 via the proximal-side opening 332, leading the one end out of the main body 31 via the hole 342*d*, inserting the one end into the main body 31 via the hole 342*e*, leading the one end out of the main body 31 via the hole 342*a*, and finally tying the one end with the other end of the string in the vicinity of the proximal-side opening 332. It is to be noted, however, that the position of the knot is not specifically restricted.

In addition, like the string 341, the string 349 is exposed outside of the main body 31 via exposure holes 345 and 346. Like the string 341, therefore, the string 349 can be cut by way of the exposure holes 345 and 346. With the string 349 laid around in this manner, the following effects can be produced. That is, in the aforementioned first embodiment, the holes 342*a*, 342*b* and 342*c* are all formed at positions near the inner circumferential portion A1, and the string 341 is also laid around near the inner circumferential portion A1. Therefore, a contracting force is exerted on the inner circumferential portion A1 side, and the main body 31 may be deformed so that those portions of the separable pieces 32 and 33 which are located on the outer circumferential portion A2 side are spaced away from each other. Upon such a deformation, a gap or a large step may be formed at the boundary between the separable pieces 32 and 33, possibly influencing the puncture of a living body. In view of this problem, in this embodiment, the hole 342*d* near the inner circumferential portion A1 of the proximal separable piece 33 and the hole 342*e* near the outer circumferential portion A2 of the distal separable piece 32 are formed, and the string 349 is laid around through these holes. As a result, such a deformation as aforementioned can be inhibited, and the main body 31 can be maintained in a predetermined shape.

According to the fourth embodiment as above, also, the same or equivalent effects to those of the aforementioned first embodiment can be produced.

Note that while the two strings 341 and 349 are used in the state maintaining mechanism 34C in this embodiment, these strings may be integrated into one (string 341). In this case, the string 341 can be obtained, for example, by inserting one end of a string (which has ends) into the main body 31 via the proximal-side opening 332, leading the one end out of the main body 31 via the hole 342*d*, inserting the one end into the main body 31 via the hole 342*e*, leading the one end out of the main body 31 via the hole 342*b*, inserting the one end into the main body 31 via the hole 342*c*, leading the one end out of the main body 31 via the hole 342*a*, and finally tying the one end with the other end of the string in the vicinity of the proximal-side opening 332.

Figure 31:
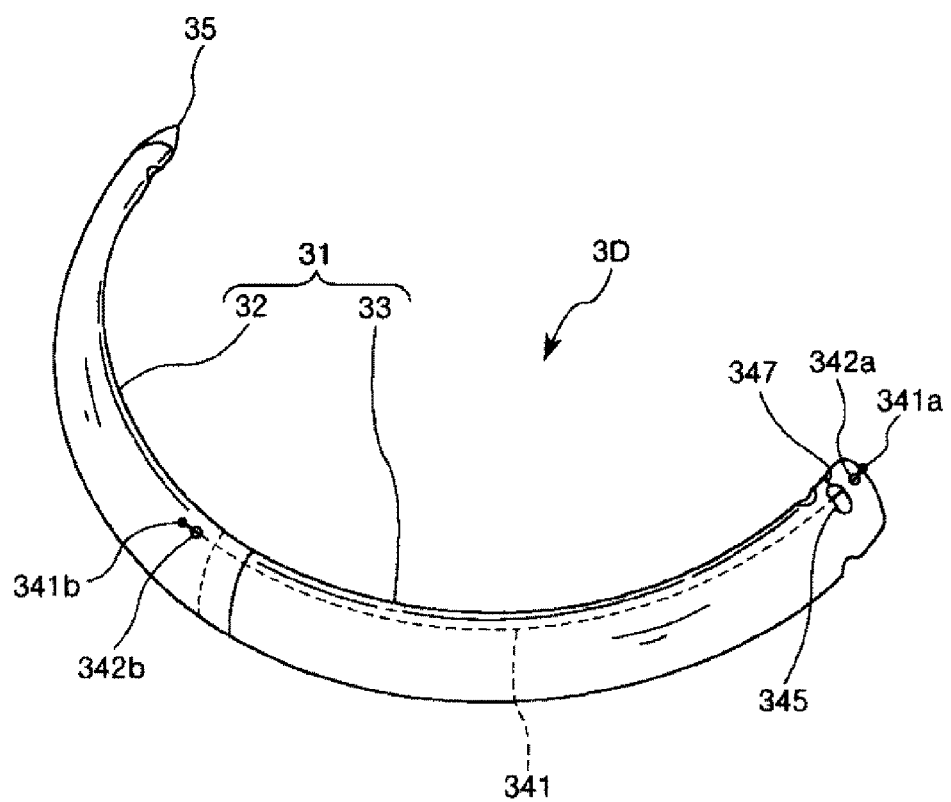
FIG. 31 is a perspective view showing a medical tube (medical tube assembly) according to a fifth embodiment of the present disclosure.

Referring to FIG. 31, the fifth embodiment of a puncture device will be described below. The following description will center on differences from the aforementioned embodiments, and descriptions of the same items as above will be omitted.

This embodiment is the same as the aforementioned first embodiment, except mainly for differences in the configuration of puncture member.

As shown in FIG. 31, a state maintaining mechanism 34D possessed by a puncture member 3D in this embodiment is configured by omitting the hole 342*c* from the state maintaining mechanism 34 in the aforementioned first embodiment, and using a string 341 which has ends. The string 341 is disposed inside a main body 31. One end of the string 341 protrudes from a hole 342*a*, and a knot 341*a* is formed at the protruding portion. The knot 341*a* is so sized as to be unable to pass through the hole 342*a*. In accordance with an exemplary embodiment, the other end of the string 341 protrudes from a hole 342*b*, and a knot 341*b* is formed at the protruding portion. The knot 341*b* is so sized as to be unable to pass through the hole 342*b*. The state maintaining mechanism 34G has the string 341 disposed in this manner, whereby a connected state of a distal separable piece 32 and a proximal separable piece 33 is maintained.

According to the fifth embodiment as above, also, the same or equivalent effects to those of the aforementioned first embodiment can be produced.

Figure 32:
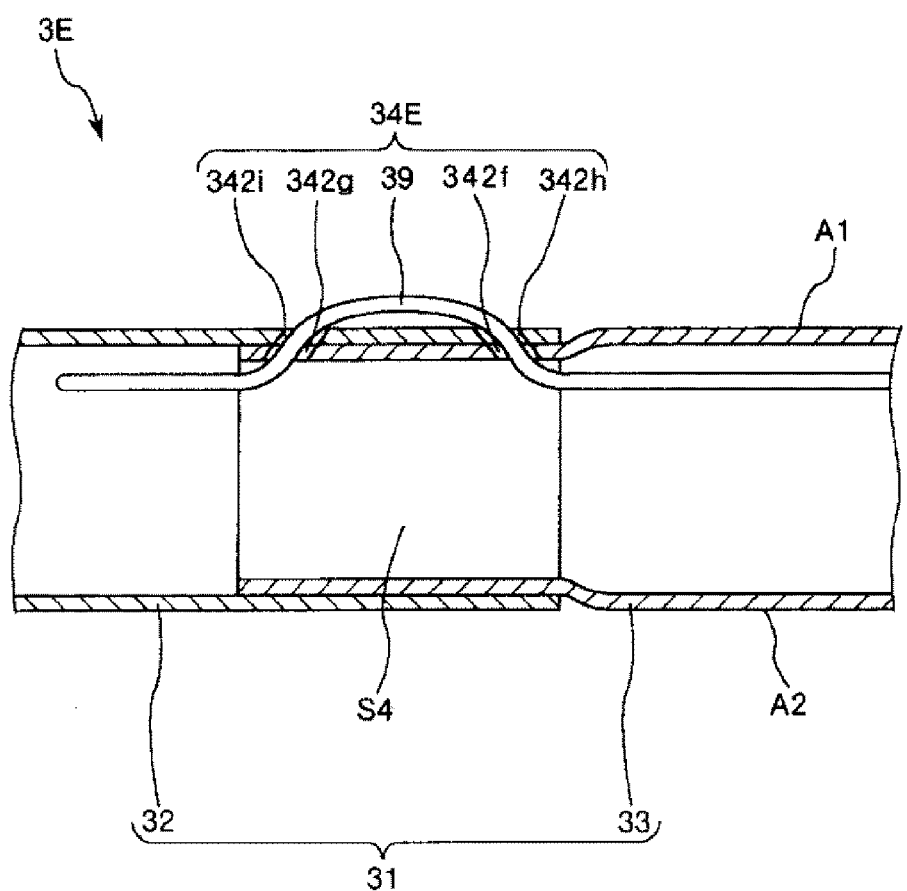
FIG. 32 is a sectional view showing a medical tube (medical tube assembly) according to a sixth embodiment of the present disclosure.

Referring to FIG. 32, the sixth embodiment of a puncture device will be described below. The following description will center on differences from the aforementioned embodiments, and descriptions of the same items as above will be omitted.

This embodiment is the same as the aforementioned first embodiment, except mainly for differences in the configuration of puncture member.

As shown in FIG. 32, a state maintaining mechanism 34E possessed by a puncture member 3E in this embodiment can include holes 342*f* and 342*g*, 342*h* and 342*i*, and a wire (linear element) 39 which is elastic and passed through the holes 342*f* and 342*g*, 342*h* and 342*i*.

The holes 342*f* and 342*g* are provided in a distal portion of an inner circumferential portion A1 of a proximal separable piece 33, juxtaposely in the axial direction. The holes 342*h* and 342*i* are provided in a proximal portion of the inner circumferential portion A1 of a distal separable piece 32, juxtaposely in the axial direction. In addition, the holes 342*f* and 342*h* are overlapping with each other, and the holes 342*g* and 342*i* are overlapping with each other. The wire 39 is led out of a main body 31 via the holes 342*f* and 342*h*, and led into the main body 31 via the holes 342*g* and 342*i*. By this, a connected state of the separable pieces 32 and 33 is maintained. Note that in the state maintaining mechanism 34E, drawing out the wire 39 via a proximal-side opening of the main body 31 results in a state in which the separable pieces 32 and 33 can be separated apart.

The wire 39 is not particularly limited. For example, wires formed of various metallic materials such as stainless steel, cobalt alloys, nickel alloys, etc. and wires composed of piano wire can be used as the wire 39.

According to the sixth embodiment as above, also, the same or equivalent effects to those of the aforementioned first embodiment can be produced.

Figure 33A:
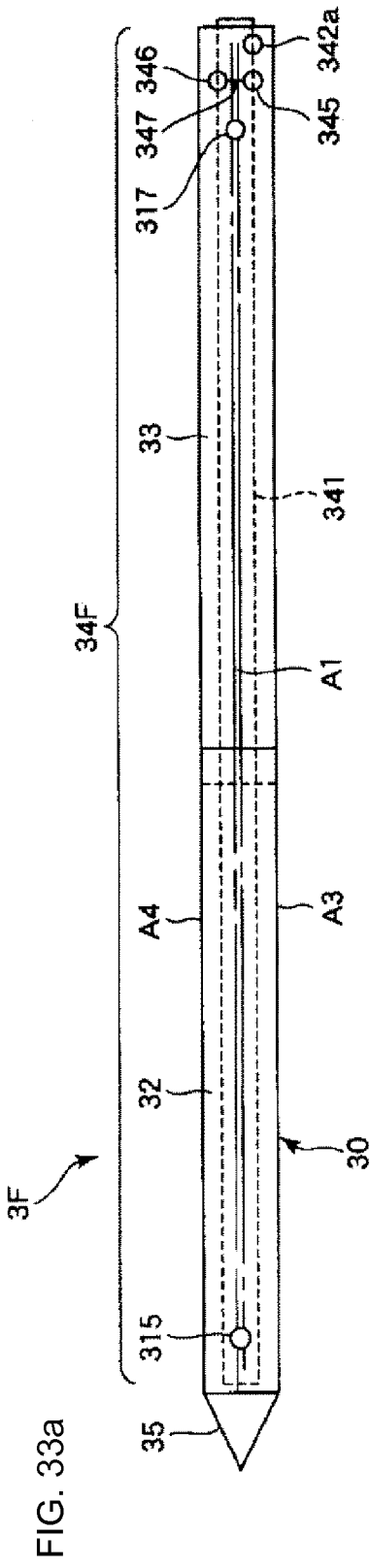
Figure 33C:
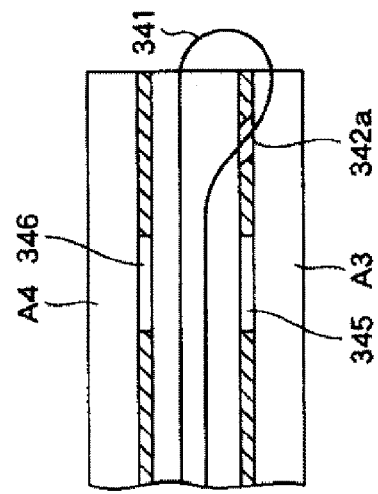
Figure 33B:
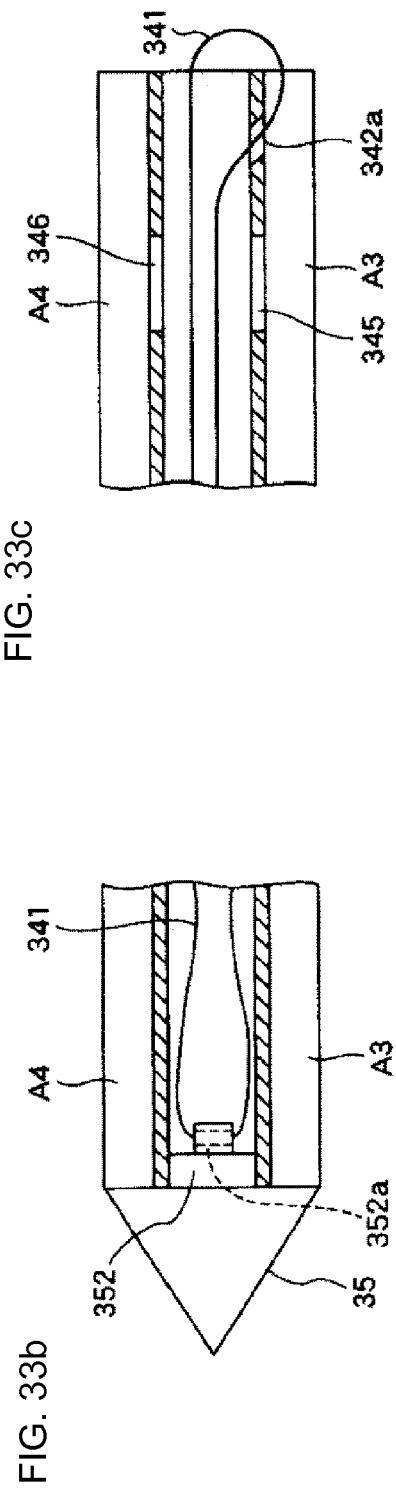

Referring to FIGS. 33(*a*)-33(*c*), the seventh embodiment of a puncture device will be described below. Note that in FIGS. 33(*a*)-33(*c*), for convenience of explanation, a puncture member extending in a circular arc shape is depicted in the state of being stretched rectilinearly. The following description will center on differences from the aforementioned embodiments, and descriptions of the same items as above will be omitted.

This embodiment is the same as the aforementioned first embodiment, except mainly for differences in the configuration of puncture member.

As shown in FIGS. 33(*a*)-33(*c*), a state maintaining mechanism 34F possessed by a puncture member 3F in this embodiment can include a hole 342*a*, a hole 352*a* provided in a proximal section 352 of a needle body 35, and a string 341. The string 341 is disposed inside a main body 31, is passed through the hole 352*a* to be thereby engaged with the needle body 35, and is passed through the hole 342*a* to be thereby engaged with a proximal separable piece 33. This configuration ensures that a state where a distal separable piece 32 is clamped between the proximal separable piece 33 and the needle body 35 can be maintained, so that a connected state of the separable pieces 32 and 33 can be maintained. Note that in the state maintaining mechanism 34F, cutting the string 341 results in a state where the separable pieces 32 and 33 can be separated apart from each other.

Note that the string 341 can be obtained, for example, by preparing a string which has ends, inserting one end of the string into the main body 31 via a proximal-side opening 332, passing the one end through the hole 352a, leading the one end out of the main body 31 via the hole 342a, and finally tying the one end with the other end of the string in the vicinity of the proximal-side opening 332.

According to the seventh embodiment as above, also, the same or equivalent effects to those of the aforementioned first embodiment can be produced.

Figure 34:
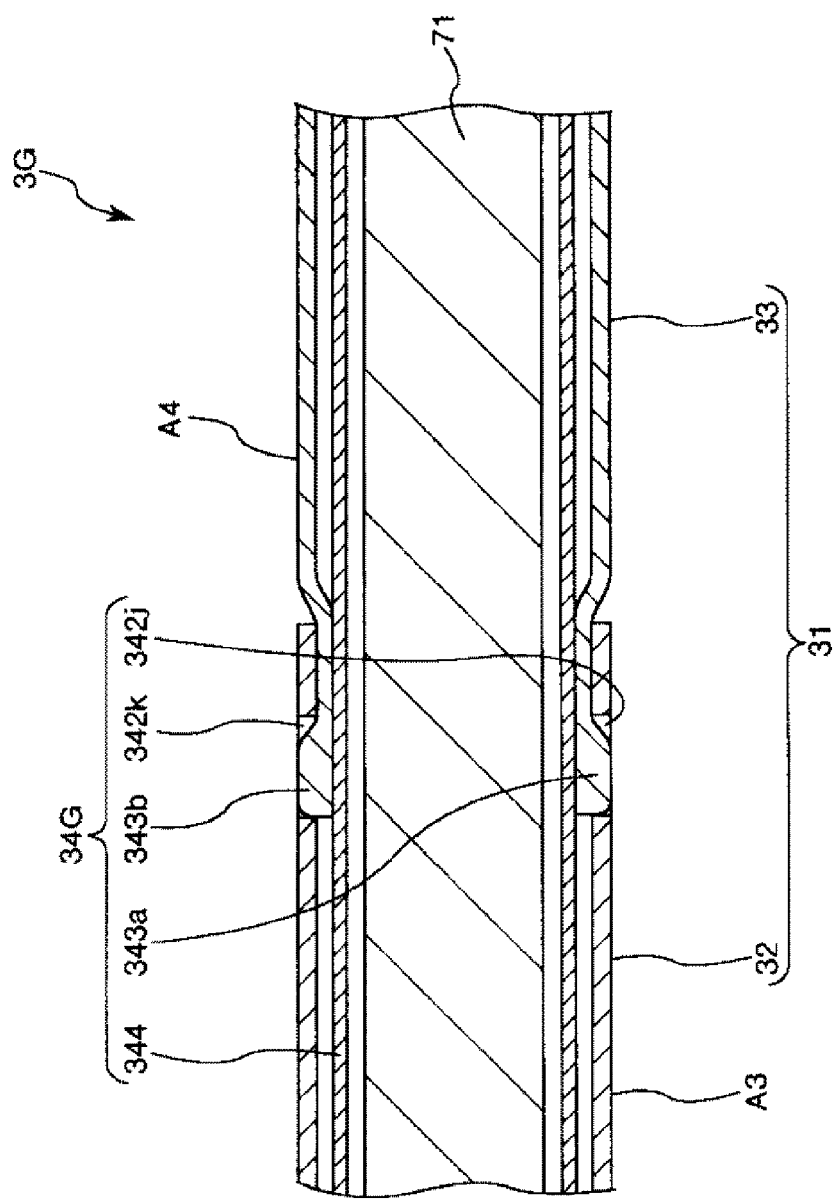
FIG. 34 is a sectional view showing a medical tube (medical tube assembly) according to an eighth embodiment of the present disclosure.
Figure 35:
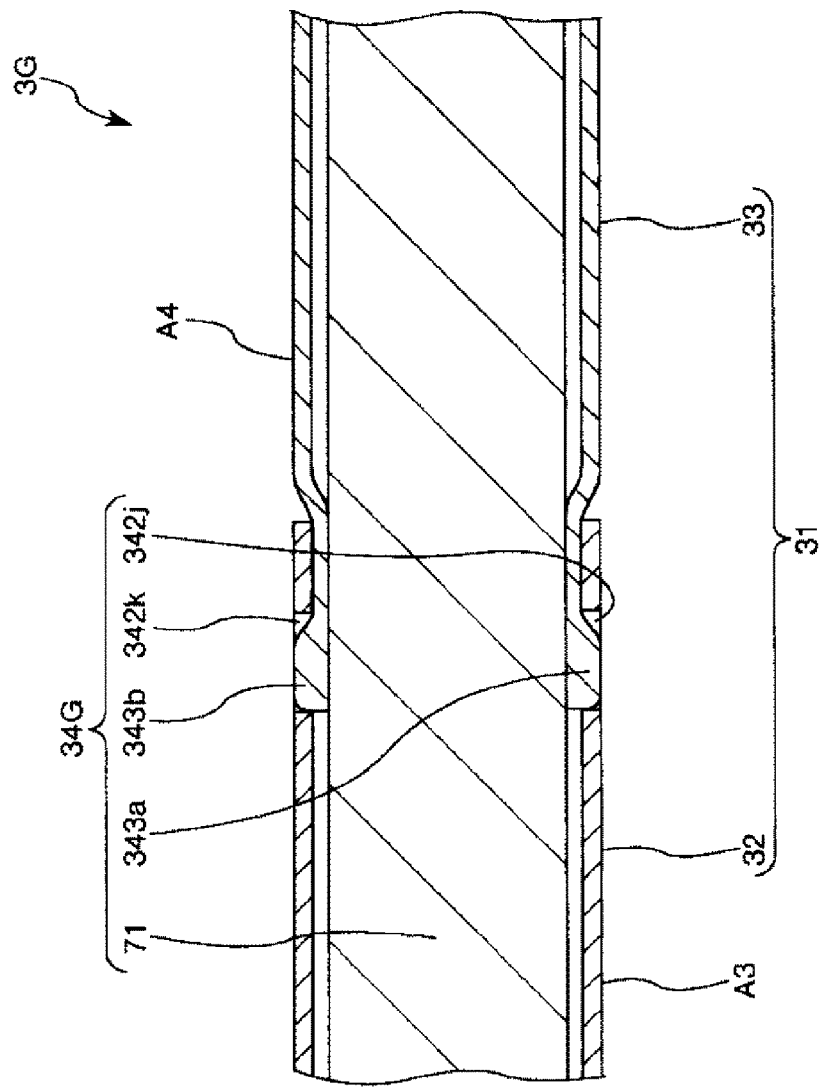
FIG. 35 is a sectional view showing a modification of the medical tube shown in FIG. 34.

Referring to FIGS. 34 and 35, the eighth embodiment of a puncture device will be described below. The following description will center on differences from the aforementioned embodiments, and descriptions of the same items as above will be omitted.

This embodiment is the same as the aforementioned first embodiment, except mainly for differences in the configuration of puncture member.

As shown in FIG. 34, a state maintaining mechanism 34G possessed by a puncture member 3G in this embodiment can include holes 342j and 342k provided in a distal separable piece 32; projections 343a and 343b provided as parts of a proximal separable piece 33; and a stylet (tubular body) 344 inserted in a main body 31. The holes 342j and 342k are separately formed in a front surface A3 and a back surface A4 of a proximal portion of the distal separable piece 32. In accordance with an exemplary embodiment, the projections 343a and 343b are separately provided as parts of the front surface A3 and the back surface A4 of a distal portion of the proximal separable piece 33. The projection 343a is in engagement with the hole 342j, and the projection 343b is in engagement with the hole 342k. In addition, the stylet 344 is inserted in the main body 31, and inward displacement of the projections 343a and 343b is restrained by the stylet 344. This configuration also ensures that a connected state of the separable pieces 32 and 33 can be maintained. Note that in the state maintaining mechanism 34G, drawing the stylet 344 out of the main body 31 to establish a state where the projections 343a and 343b can be displaced inward results in a state in which the separable pieces 32 and 33 can be separated apart from each other.

The material constituting the stylet 344 is preferably a rigid material such that displacement of the projections 343a and 343b can be restrained thereby. Examples of the rigid material usable include various resin materials such as polyethylene, polyimides, polyamides, polyester elastomers, polypropylene, and various metallic materials such as stainless steel, aluminum or aluminum alloys, titanium or titanium alloys. Note that the configuration of the stylet 344 can be achieved not only by the adoption of the rigid material but also by adopting other material than rigid material and reinforcing a wall of the stylet with a reinforcement member.

According to the eighth embodiment as above, also, the same or equivalent effects to those of the aforementioned first embodiment can be produced.

Note that while the state maintaining mechanism 34G has the stylet 344 in this embodiment, a configuration may be adopted in which an insertion section 71 inserted in the main body 31 functions also as a stylet 344 as shown in FIG. 35. In accordance with an exemplary embodiment, a configuration may be adopted in which inward displacement of the projections 343a and 343b is restrained by the insertion section 71.

Figures 36A, 36B, 36C:
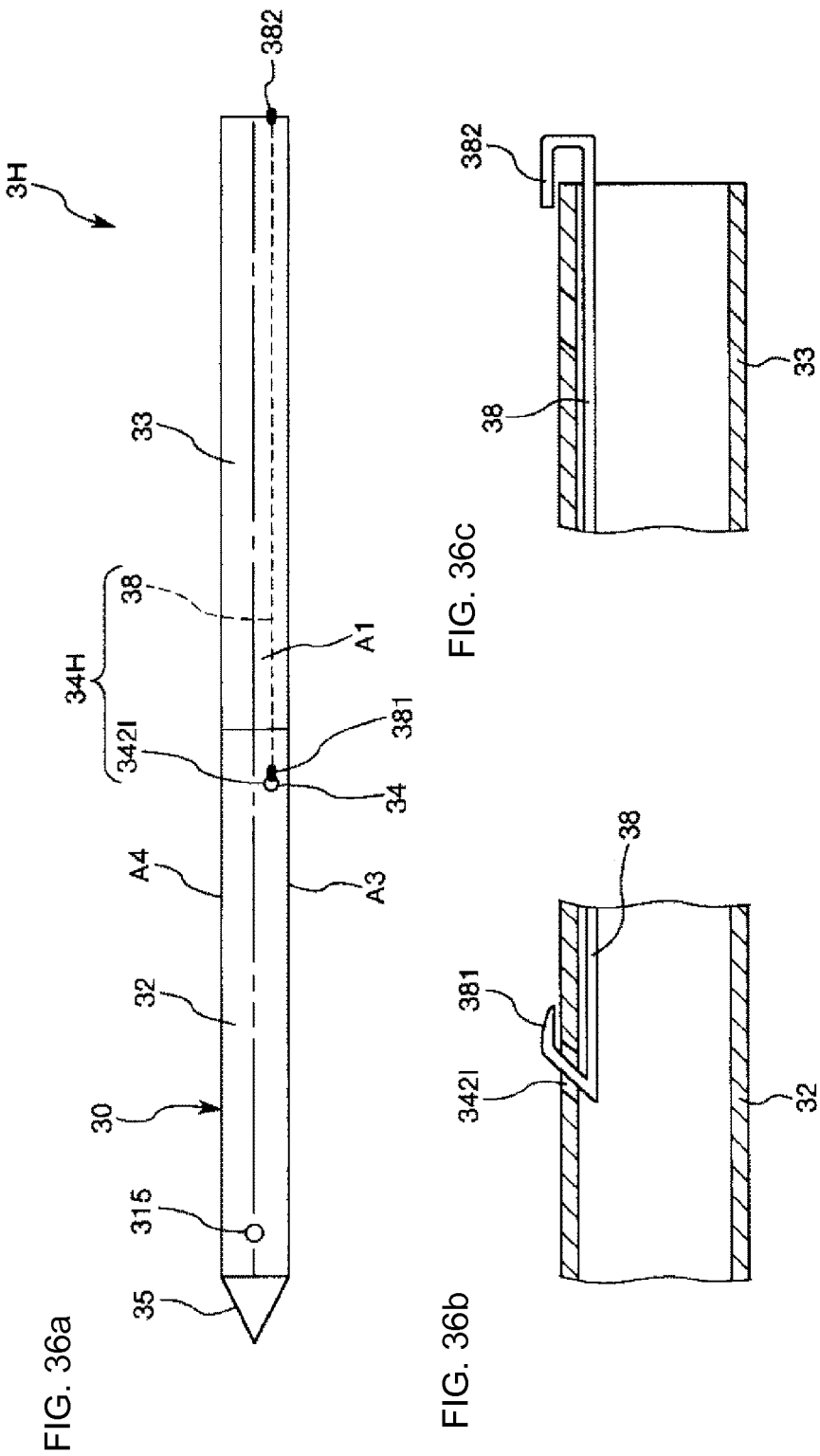

Referring to FIGS. 36(a)-36(c), the ninth embodiment of a puncture device will be described below. Note that in FIGS. 36(a)-36(c), for convenience of explanation, a puncture member extending in a circular arc shape is depicted in the state of being stretched rectilinearly. The following description will center on differences from the aforementioned embodiments, and descriptions of the same items as above will be omitted.

This embodiment is the same as the aforementioned first embodiment, except mainly for differences in the configuration of puncture member.

As shown in FIGS. 36(a)-36(c), a state maintaining mechanism 34H possessed by a puncture member 3H in this embodiment can include a hole 342I provided in a distal separable piece 32, and an elastic wire 38. The wire 38 is provided at a distal portion thereof with a distal hook (claw section) 381 hooked on the hole 342I, and is provided at a proximal portion with a proximal hook (claw section) 382 hooked on the proximal end of a proximal separable piece 33. With the distal hook 381 and the proximal hook 382 hooked respectively on the hole 342I and the proximal separable piece 33, a connected state of the separable pieces 32 and 33 can be maintained. Note that in the state maintaining mechanism 34H, pushing in the wire 38 toward the distal side to evacuate the distal hook 381 into a main body 31 and thereby disengaging the distal hook 381 and the hole 342I from each other results in a state in which the separable pieces 32 and 33 can be separated apart from each other.

According to the ninth embodiment as above, also, the same or equivalent effects to those of the aforementioned first embodiment can be produced.

While the medical tube, medical tube assembly and intrapelvic treatment kit of the present disclosure have been described above on the basis of the illustrated embodiments, the present disclosure is not limited to the embodiments. The configuration of each component can be replaced with an arbitrary configuration having the same or equivalent function. In accordance with an exemplary embodiment, other arbitrary structure or structures may be added to the present disclosure.

In addition, while the needle body is retained on the main body in an attachable and detachable manner in the above embodiments, this configuration is not restrictive. For example, the needle body may be fixed to the main body, like in a configuration wherein the main body and the needle body are formed integrally. In this case, the distal-side opening of the main body can be opened by cutting the needle body by use of a pair of scissors or the like, after a living body is punctured by the puncture member and the needle body is protruded to the outside of the living body.

In accordance with an exemplary embodiment, while a configuration wherein the main body can be separated into the distal separable piece and the proximal separable piece has been described in the aforementioned embodiments, the configuration of the main body is not limited to the described. The main body may be so configured that it cannot be separated to the distal side and the proximal side. In accordance with an exemplary embodiment, the main body may be configured as a single tubular body. In this case, the state maintaining mechanism is omitted.

In addition, while the sheath is configured as part of the puncture member in the above embodiments, this configuration is not restrictive. In accordance with an exemplary embodiment, a sheath may be used in the manner of being inserted into a penetrating hole preliminarily formed in a living body by use of some means. Specifically describing in correspondence with the aforementioned first embodiment, a puncture device 1 with the puncture member 3 omitted therefrom is prepared, an insertion section 71 is used as a puncture member, and its distal portion 711 is made to puncture an inguinal region on the right side of the patient, to sequentially pass an obturator foramen on one side, between the urethra and the vagina, and an obturator foramen on the other side, and then to exit the living body via an inguinal region on the left side. Next, the insertion section 71 is inserted into the inside, and a sheath 30 (main body 31) is advanced into the body along the insertion section 71, resulting in a state where both ends of the sheath 30 are protruding from the body surface H. Subsequently, the insertion section 71 is drawn out of the body. As a result, the sheath 30 is disposed inside the living body. Then, an implant main body is disposed inside the sheath 30, and the sheath 30 is drawn out of the body, whereby the implant main body can be placed indwelling in the living body, like in the aforementioned embodiments.

In accordance with an exemplary embodiment, for example, the distal portion 711 of the insertion section 71 is made to puncture the inguinal region on the right side of the patient, to sequentially pass the obturator foramen on one side, between the urethra and the vagina, and the obturator foramen on the other side, and to protrude to the outside of the body via the inguinal region on the left side, and thereafter a distal portion of the sheath 30 is fixed to the distal portion 711. Next, the distal portion 711 is rotated in the opposite direction, to draw the insertion section 71 out of the body, and the sheath 30 is left indwelling in the living body. Then, the implant main body is disposed inside the sheath 30, and the sheath 30 is drawn out of the body, whereby the implant main body can be placed indwelling in the living body, like in the aforementioned embodiments.

In addition, while a configuration wherein the main body of the puncture member is disposed inside a living body and thereafter the implant main body is inserted into the main body has been described in the above embodiments, this configuration is not restrictive. A configuration may be adopted in which the implant main body is accommodated in the puncture member (main body) from the beginning. In this case, it is preferable that, for example, a string located on the needle tip side, of two strings possessed by the implant main body, is preliminarily fixed to the needle tip, which can help ensure that when the needle tip is detached from the main body, the string can be protruded to the outside of the main body in an attendant manner. As a result, the subsequent fine adjustment of the disposition of the implant main body and the like can be performed smoothly.

In accordance with an exemplary embodiment, while a case where the puncture device is applied to a device for use in embedding in a living body an embeddable implant for treatment of female urinary incontinence has been described in the above embodiments, the use of the puncture device is not limited to the described one.

For example, the target of the application of the present disclosure can include excretory disorders as a result on the weakening of the pelvic floor muscle group (urinary urgency, frequent urination, urinary incontinence, fecal incontinence, urinary retention, or dysuria), and pelvic floor disorders including pelvic organ prolapse, vesicovaginal fistula, urethrovaginal fistula, pelvic pain or the like. In the pelvic organ prolapse, there are included disorders of cystocele, enterocele, rectocele, uterine prolapse and the like. Alternatively, there are included such disorders as anterior vaginal prolapse, posterior vaginal prolapse, vaginal apical prolapse, vaginal vault prolapse and the like in which the naming method thereof is based on the prolapsed vaginal-wall part.

Also, overactive tissues include bladder, vagina, uterus, bowel and the like. Lessactive tissues include bones, muscles, fascias, and ligaments. In accordance with an exemplary embodiment, in the case of pelvic floor disorders, the lessactive tissues include an obturator fascia, a coccygeus fascia, a cardinal ligament, an uterosacral ligament, and a sacrospinous ligament.

For the procedure for interlocking an overactive tissue in the pelvic floor disorder with the lessactive tissue, there are included a retropubic sling surgery, a transobturator sling surgery (transobturator tape (TOT) surgery), a tension-free vaginal mesh (TVM) surgery, a uterosacral ligament suspension (USLS) surgery, a sacrospinous ligament fixation (SSLF) surgery, an iliococcygeus fascia fixation surgery, a coccygeus fascia fixation surgery, and the like.

The medical tube of the present disclosure can include a tubular main body having a curved central portion, and is characterized in that the central portion is circular arc shaped at least at part thereof, the main body has a flat shape including a minor axis and a major axis as a cross-sectional shape at the central portion, and the angle formed between the minor axis and a plane containing both a center point of the circular arc in the central portion and a center point of the cross-sectional shape with respect to the longitudinal direction of the main body is an acute angle. For example, at the time of disposing the main body in a body in the manner of sequentially passing the obturator foramen on one side, between the urethra and the vagina, and the obturator foramen on the other side, the insertion of the main body into the living body can be carried out easily and safely by a method in which the angle formed between the above-mentioned plane and a plane orthogonal to the axis of the urethra is set to be an acute angle (at the same degree as the above-mentioned angle). Therefore, when the angle formed between the above-mentioned plane and the minor axis is set to be an acute angle, the main body can be disposed in the living body so that the major axis direction of the cross section is substantially parallel to the urethra. As a result, the implant inserted in the main body can also be disposed substantially in parallel to the urethra. Thus, according to the present disclosure, the implant can be placed indwelling in a living body in such a posture as to be able to exhibit its function effectively.

Accordingly, the medical tube of the present invention has industrial applicability.

The detailed description above describes a medical tube, a medical tube assembly and an intrapelvic treatment kit. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical tube comprising:
   a tubular main body having a curved central portion, the tubular main body composed of two separable pieces, which are separable in the curved central portion;
   at least part of the curved central portion having a circular arc shape; and
   the tubular main body having a flattened circular shape including a minor axis in a direction of a front surface and a back surface and a major axis in a direction of an inner circumferential portion and an outer circumferential portion as a cross-sectional shape at the central portion, the inner circumferential portion and the outer circumferential portion being spaced apart from each other in a direction of a center axis and an angle formed between the minor axis and a plane containing both a center point of the circular arc in the central portion and a center point of the cross-sectional shape with respect to a longitudinal direction of the tubular main body being an acute angle.

2. The medical tube according to claim 1, wherein the acute angle is 20° to 60°.

3. A medical tube assembly comprising:
the medical tube according to claim 1; and
an elongated insertion section to be inserted into the tubular main body,
wherein the medical tube assembly is used in a state where the insertion section is inserted in the tubular main body.

4. The medical tube according to claim 1, wherein each of the two separable pieces of the tubular main body is of a same length.

5. A medical tube for use in intrapelvic treatment, comprising:
a tubular main body having an internal space configured to receive an elongated article, the tubular main body having a curved central portion, and wherein the tubular main body is composed of two separable pieces, which are separable in the curved central portion;
at least part of the central portion having a circular arc shape, the tubular main body having a flattened circular shape including a minor axis in a direction of a front surface and a back surface and a major axis in a direction of an inner circumferential portion and an outer circumferential portion as a cross-sectional shape at the central portion, the inner circumferential portion and the outer circumferential portion being spaced apart from each other in a direction of a center axis;
the center axis of the circular arc of the circular arc shape and an extension line of the major axis having an intersection; and
wherein an angle formed between the center axis and the extension line is an acute angle of 20° to 60°.

6. The medical tube according to claim 5, wherein the tubular main body is formed from a rigid material capable of maintaining the internal space in a state where the tubular main body is inserted in a living body.

7. The medical tube according to claim 5, wherein each of the two separable pieces of the tubular main body is of a same length.

8. An intrapelvic treatment kit characterized by comprising:
an implant main body having a width and a length; and
a medical tube including a main body which is tubular in shape, the main body having a curved central portion and an internal space, the main body composed of two separable pieces, which are separable in the curved central portion, and the central portion having a circular arc shape at least at part of the central portion, and the main body having a flattened circular shape including a minor axis in a direction of a front surface and a back surface and a major axis in a direction of an inner circumferential portion and an outer circumferential portion as a cross-sectional shape at the central portion, the inner circumferential portion and the outer circumferential portion being spaced apart from each other in a direction of a center axis, and wherein a length of the major axis in the internal space is shorter than the width of the implant main body, and wherein an angle formed between the minor axis and a plane containing both a center point of the circular arc in the central portion and a center point of the cross-sectional shape with respect to a longitudinal direction of the main body is an acute angle.

9. The kit according to claim 8, wherein the acute angle is 20° to 60°.

10. The kit according to claim 8, wherein the main body is formed from a rigid material capable of maintaining the internal space in a state where the main body is inserted in a body.

11. A method for treatment of a disease in a pelvic organ by leaving an implant indwelling between a urethral lumen and a vaginal cavity, the method comprising:
inserting a medical tube into a living body, the medical tube having a tubular main body having a curved central portion, and wherein the tubular main body is composed of two separable pieces, which are separable in the curved central portion, and at least part of the central portion has a circular arc shape, and the tubular main body having a flattened circular shape including a minor axis in a direction of a front surface and a back surface and a major axis in a direction of an inner circumferential portion and an outer circumferential portion as a cross-sectional shape at the central portion, the inner circumferential portion and the outer circumferential portion being spaced apart from each other in a direction of a center axis and an angle formed between the minor axis and a plane containing both a center point of the circular arc in the central portion and a center point of the cross-sectional shape with respect to a longitudinal direction of the tubular main body being an acute angle;
inserting an implant main body into the internal space of the medical tube;
removing each of the two separable pieces of the medical tube from the living body; and
embedding the implant main body in the living body between the urethral lumen and the vaginal cavity.

12. The method according to claim 11, wherein the acute angle is 20° to 60°.

13. The method according to claim 11, comprising:
disposing the main body inside the living body in such a manner that the major axis direction of the cross section of the tubular main body is substantially parallel to the urethral lumen.

14. The method according to claim 11, wherein each of the two separable pieces of the tubular main body is of a same length and constructed of a rigid material.

* * * * *